US010869915B2

(12) United States Patent
Battesti et al.

(10) Patent No.: US 10,869,915 B2
(45) Date of Patent: Dec. 22, 2020

(54) METHOD FOR PRODUCING EMBRYONIC-LIKE STEM CELLS FROM TICKS (ACARI: IXODIDAE), COMPOSITION, USES THEREOF AND DIAGNOSTIC METHODS

(71) Applicants: BIOTICK PESQUISA E DESENVOLVIMENTO TECNOLÓGICO LTDA, Santa Paula, São Caetano do Sul-SP (BR); FUNDACÃO BUTANTAN, Butantan, São Paulo-SP (BR)

(72) Inventors: Darci Moraes Barros Battesti, Sao Paulo-SP (BR); Irina Kerkis, Sao Paulo-SP (BR); Ronaldo Zucatelli Mendonca, Sao Paulo-SP (BR); Durvanei Augusto Maria, Sao Paulo-SP (BR); Angelina Cirelli Moraes, Sao Paulo-SP (BR)

(73) Assignees: BIOTICK PESQUISA E DESENVOLVIMIENTO TECNOLÓGICO LTDA, São Caetano do Sul-SP (BR); FUNDACÃO BUTANTAN, São Paulo-SP (BR)

( * ) Notice: Subject to any disclaimer, the term of this patent is extended or adjusted under 35 U.S.C. 154(b) by 34 days.

(21) Appl. No.: 15/752,140

(22) PCT Filed: Aug. 12, 2016

(86) PCT No.: PCT/BR2016/050191
§ 371 (c)(1),
(2) Date: Feb. 12, 2018

(87) PCT Pub. No.: WO2017/024372
PCT Pub. Date: Feb. 16, 2017

(65) Prior Publication Data
US 2018/0236051 A1  Aug. 23, 2018

(30) Foreign Application Priority Data
Aug. 12, 2015  (BR) .......................... 10 2015 019426

(51) Int. Cl.
| A61K 35/64 | (2015.01) |
| A61K 39/00 | (2006.01) |
| C12N 1/10 | (2006.01) |
| C12N 1/20 | (2006.01) |
| G01N 33/53 | (2006.01) |
| A61K 35/56 | (2015.01) |
| A61K 35/646 | (2015.01) |
| A61K 39/02 | (2006.01) |
| C12N 5/07 | (2010.01) |
| C07K 14/29 | (2006.01) |

(52) U.S. Cl.
CPC .......... *A61K 39/0003* (2013.01); *A61K 35/56* (2013.01); *A61K 35/646* (2013.01); *A61K 39/00* (2013.01); *A61K 39/0233* (2013.01); *C12N 1/10* (2013.01); *C12N 1/20* (2013.01); *C12N 5/0601* (2013.01); *G01N 33/53* (2013.01); *C07K 14/29* (2013.01)

(58) Field of Classification Search
CPC ...................................... A61K 35/64
See application file for complete search history.

(56) References Cited

U.S. PATENT DOCUMENTS 4,447,537 A  5/1984 Yunker et al.

FOREIGN PATENT DOCUMENTS

BR  9610681  7/1999

OTHER PUBLICATIONS

Nava et al. (2014, Ticks and Tick-borne Diseases, vol. 5, pp. 252-276) (Year: 2014).*
Rezende et al. (2012, Braz. J. Biol., vol. 72(3), pp. 577-582) (Year: 2012).*
Ferrari et al. (2013, J. Medical Entom., vol. 50(5), pp. 1118-1125). (Year: 2013).*
International Preliminary Report on Patentability in corresponding PCT Application Serial No. PCT/BR2016/050191, dated Feb. 13, 2018, 13 pages.
Search Report in related PCT Application Serial No. PCT/BR2016/050191, dated Dec. 20, 2016 (English translation attached).
Moraes, "Establishment and characterization of embryonic cells of Amblyomma sculptum Berlese (Acari: Ixodidae)", Doctorate Degree in Biotechnology, Institute of Biomedical Sciences, University of Sao Paulo, Sao Paulo, 2015 (English translation attached).
Rezende, et al., "Primary embryonic cells of Rhipicephalus microplus and Amblyomma cajennense ticks as a substrate for the development of Borrelia burgdorferi (strain G39/40)", Braz. J. Biol., 2012, vol. 72, issue 3, pp. 577-582 (English translation attached).
Ferrari, et al., "Isolation of "Candidatus Rickettsia andeanae" (Rickettsiales: Rickettsiaceae) in embryonic cells of naturally infected Amblyomma maculatum (Ixodida: Ixodidae)", J. Med. Entomol., Sep. 2013, vol. 50, issue 5, pp. 1118-1125 (abstract attached).
Franze, "Culture of embryonic-simile cells of Rhipicephalus sanguineus (Latreille) (Acari: Ixodidae) for isolation and pathogen cultivation", Dissertation presented to the Post-Undergraduate Interunits in Biotechnology, Institute of Biomedical Sciences, University of Sao Paulo, Sao Paulo, 2014 (English abstract attached).

(Continued)

*Primary Examiner* — Thaian N. Ton
*Assistant Examiner* — David A. Montanari
(74) *Attorney, Agent, or Firm* — Hovey Williams LLP

(57) ABSTRACT

The invention refers to a process for the production of a continuous cell line of simile embryo stem cells, such as *Amblyomma sculptum* (Acari: Ixodidae), known as line IBU/ASE-16 (access number with CNCM: 1-5000) and its uses. More specifically, the invention refers to a process for the production of the line IBU/ASE-16 and their use for obtaining extracts for the production of vaccines and candidate recombinant proteins for biopharmaceuticals and acaricides, production of diagnostic kits for the detection of antigens and/or antibodies for animal and human use, obtaining clones for use in genotyping and use as a substrate for the isolation and culture of pathogens.

14 Claims, 24 Drawing Sheets

(56) References Cited

OTHER PUBLICATIONS

Cirelli-Moraes, et al., "Primary Culture of Embryonic Cells of Amblyomma cajennense, Amblyomma dubitatum, Amblyomma rotundatum, Ixodes schulzei and Rhipicephalus sanguineus (Acari: Ixodidae)", XIII International Congress of Acarology, Aug. 23-27, 2010, p. 57 (abstract attached).
Varela, et al., "First Culture Isolation of Borrelia Ionestari, Putative Agent of Southern Tick-Associated Rash Illness", J.Clin. Microbiol., Mar. 2004, vol. 42, issue 3, pp. 1163-1169.
Kurtii, et al., "Factors influencing in vitro infectivity and growth of Rickettsia peacockii (Rickettsiales: Rickettsiaceae), an endosymbiont of the Rocky Mountain wood tick, *Dermacentor andersoni* (Acari, Ixodidae)", J. Invertebr. Pathol., Nov. 2005, vol. 90, issue 3, pp. 177-186 (abstract attached).

\* cited by examiner

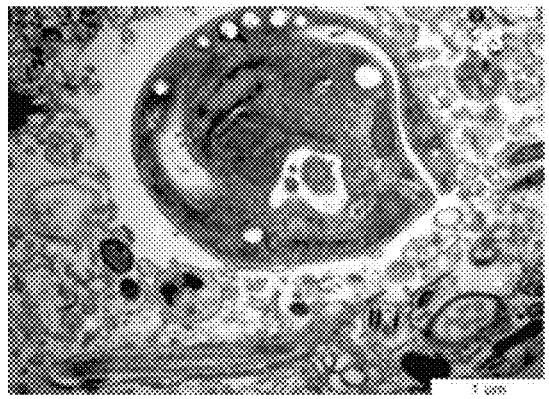
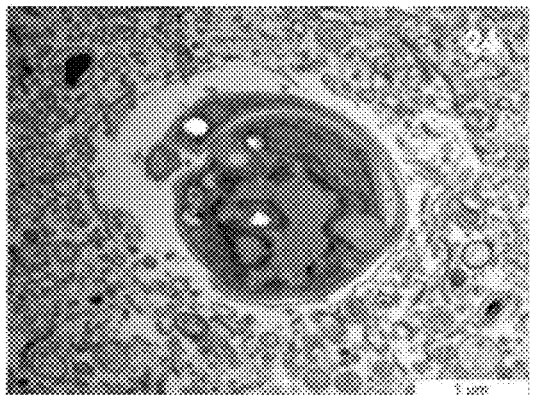
Figure 23                    Figure 24
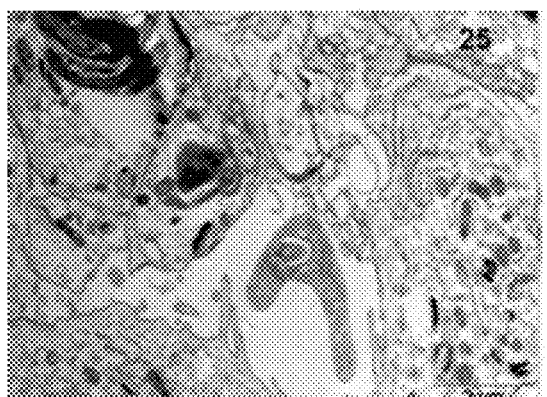
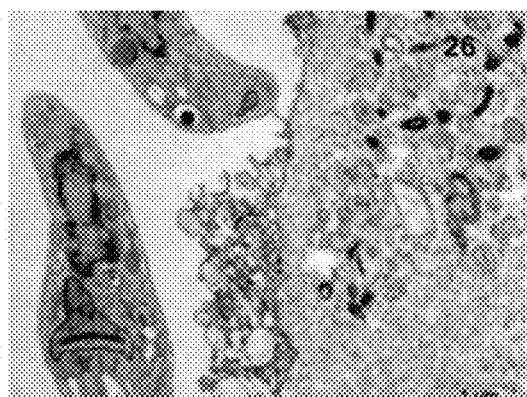
Figure 25                    Figure 26
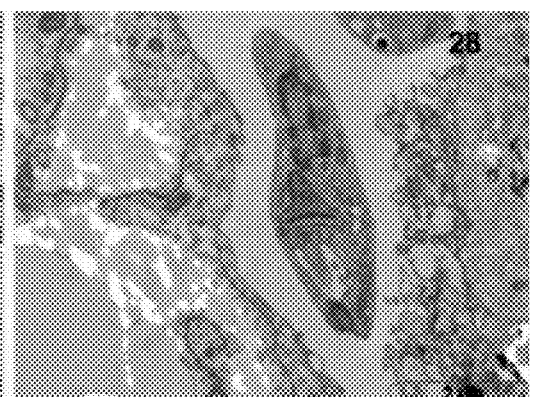
Figure 27                    Figure 28

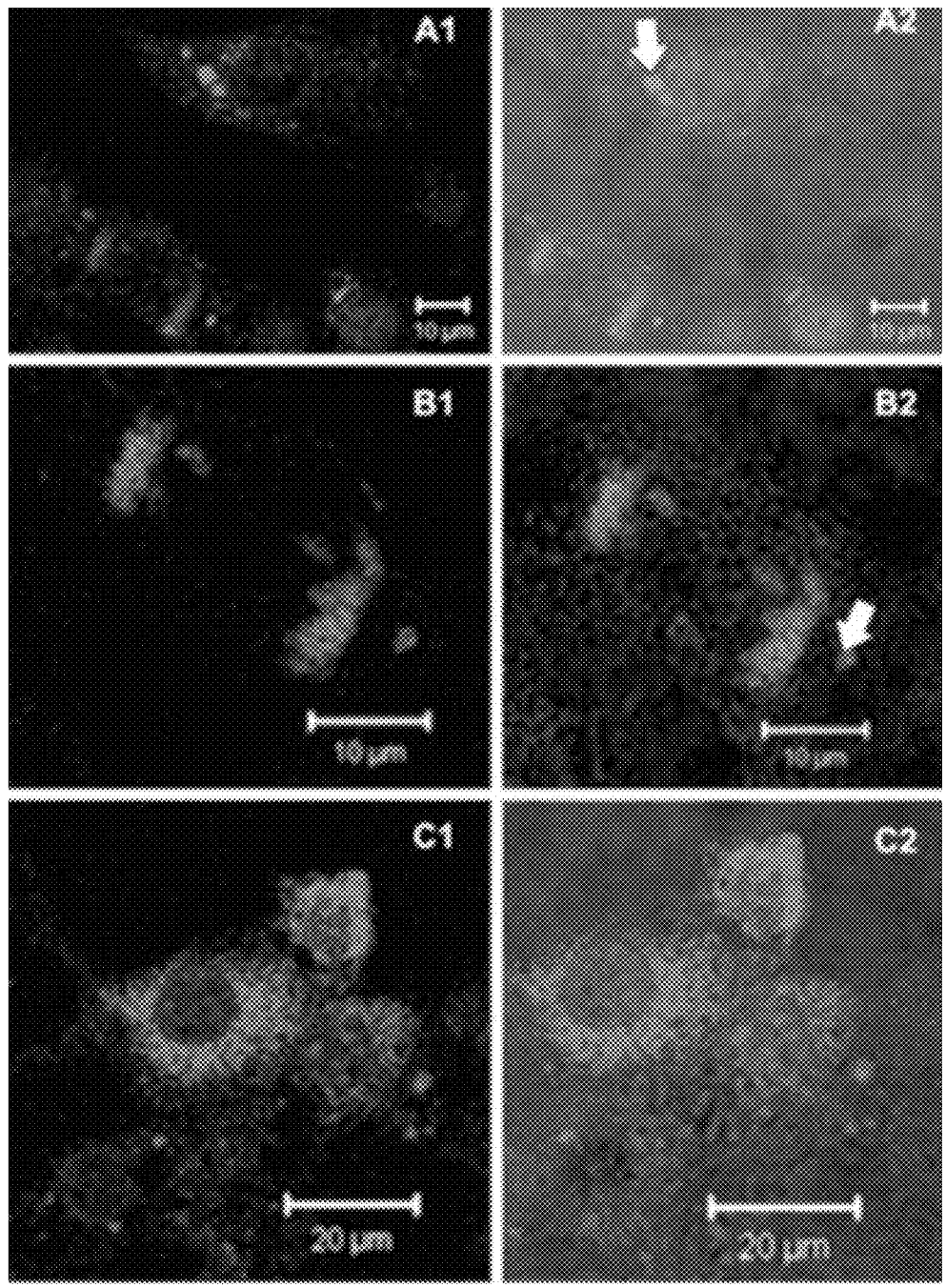
Figure 40 – A - C

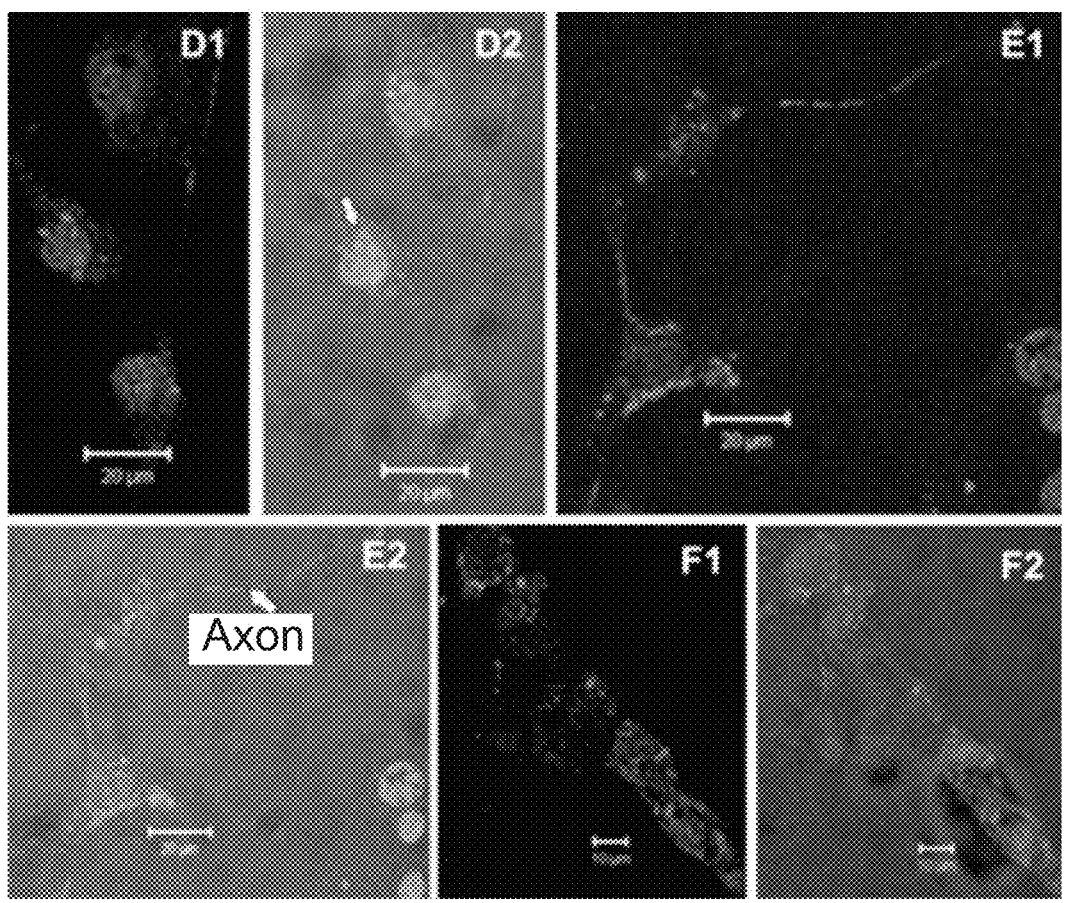
Figure 40 – D - F

Figure 52

```
TTA  72

Query  299
AGTTTAAAAAAGATTTTTTCTGTTATTCCATTCTCTTAGCACTCAATTAAAGTCTTA
TT-  357
              |  ||||||||||  |||||||||
|||||||||||||||||||||||||||||||||||||||
Sbjct  71
AATTTAAAAAAGCTTTTTTCTGTAATTCCATTCTCTTAGCACTCAATTAAAGTCTTA
TTT  12

Query  358    CAATACCTT   366
              |||||||||
Sbjct  11    CAATACCTT   3
```

Figure 52 (continued)

METHOD FOR PRODUCING EMBRYONIC-LIKE STEM CELLS FROM TICKS (ACARI: IXODIDAE), COMPOSITION, USES THEREOF AND DIAGNOSTIC METHODS

RELATED APPLICATIONS

The present application is the U.S. National Stage of International Patent Application No. PCT/BR2016/050191, filed Aug. 12, 2016, which is hereby incorporated by reference in its entirety, and which claims priority to Brazilian Patent Application No. BR 10 2015 019426-9, filed Aug. 12, 2015.

FIELD OF THE INVENTION

The invention refers to a process for the production of continued lines of simile embryo stem cells and their composition, which are obtained from embryo eggs e.g. from *Amblyomma scuptum* (Berlese, 1888). The invention also refers to the use of those cells or cell lines characterized for micro-organism replication. More specifically, the invention refers to the use of these cells, composition or its cell lines and cell clones, for the production of vaccines, diagnostic kits for the detection of antibodies and antigens, both human and animal, isolation and characterization of different kinds of precursor cells, e.g. neuronal or any others, or even differentiated cells, if required, and obtaining clones for use in genotyping (biomarkers).

BACKGROUND OF THE INVENTION

After mosquitoes, ticks are the main pathogen vectors. However, they invert positions when the devastating impacts caused by ticks are analyzed.

Ectoparasites and hematophagous, ticks are not only responsible for relevant economic loss, but also for damage to human and animal health, by transmitting virus, bacteria and protozoa. Various microorganisms do not grow on artificial media. Therefore, embryo cell lines from ticks have been established with the purpose to serve as a substrate for the growth and isolation of those pathogens.

Simile embryo stem cells (ESC) from ticks and their continued lines are becoming an important and exceptional tool, in many aspects, for the research of pathogen-transmitting ticks, and also for studying the biology of those arthropods, in host-vector-pathogen relations, disease control, genomics, proteomics and genetic manipulations, thus showing the great application potential for those lines. Furthermore, ESC lines are essential tools for the development and enhancement of various technologies, such as: expression of proteins of interest; vaccines; antigen production; maintenance of microorganisms, selective screening of drugs and pharmaceuticals for human and veterinary use; genotyping; detection of biomarkers and study of neurologic, neurodegenerative and autoimmune diseases, among others.

The initiation of a primary culture from embryo tissues from ticks, for the future establishment of a cell line, is a difficult task. Cell lines from arthropods of the class Insecta have been successfully established, in opposition to the low establishment of cell lines from Arachnida, especially with reference to the subclass Acari (mites and ticks), and much less to the family Ixodidae, which is a larger and more representative group among ticks. This fact is widely explained for a few reasons: tick cells are extremely fragile and challenging. Each species has its peculiarities, such as an appropriate means of culture, supplements, initiation period for the primary culture, and others. As a consequence of these requirements, the same protocol may not always be used for different species.

The first studies with tick cell cultures have been performed in the 1950s by Weyer (1952), obtaining cells from *Rhipicephalus bursa* tissues Canestrini & Fanzago, with a culture lasting just eight days.

Other cell cultures from different tick species have been subsequently obtained, such as: *Hyalomma dromedarii* Koch, *Hyalomma anatolicum excavatum* Koch, *Rhipicephalus sanguineus* (Latreille), *Rhipicephalus appendiculatus* Neumann, *Dermacentor marginatus* (Sulzer), *Dermacentor reticulatus* (Fabricius) (=*Dermacentor pictus*), *Dermacentor andersoni* Stiles, *R. annulatus* (referred to as *Boophilus annulatus*), *Rhipicephalus* (*Boophilus*) *decoloratus* (Koch) (referred to as *Boophilus decoloratus*), *R. microplus* (referred to as *Boophilus microplus*) and *I. ricinus* (PUDNEY et al, 1973).

On the other hand, cells obtained from embryo tissues of *Hyalomma asiaticum asiaticum* Schulze & Schlottke were obtained up to the tenth passage (MEDVEDEVA et al, 1972). Pudney et al (1973) cultivated cells derived from embryo tissues of *R. microplus* until the twentieth passage, but, according to those authors, after the last passage, cells reached the senescence step, i.e. they got old and deteriorated. From all those species as mentioned, only *R. microplus* and *R. sanguineus* are found in Brazil.

Despite considerable progress from the first works to the early 1970s, the success of cultures of tick cells in vivo was limited to primary cultures. Varma et al (1975) established the three primary cultures of line cells (TTC-219, TTC-243 and TTC-257) from *R. appendiculatus* ticks. Bhat & Yunker (1977) established line cells RML-14, using cells derived from embryo tissues of *Dermacentor parumapertus*, Neumann. Four years later, six new lines (RML-15, RML-16, RML-17, RML-18, RML-19 and RML-20), limited by the number of replications in vitro, were established by Yunker et al (1981) from embryo tissues of *Dermacentor variabilis* Say and *D. parumapertus*. After a decade, Bell-Sakyi (1991) established five new lines (HAE CT VM 7, HAE CT VM 8, HAE CT VM 9, HAE CT VM 10, HAE CT VM 11) from embryo tissues of *Hyalomma anatolicum anatolicum* Koch.

Munderloh et al (1994) disclosed a method allowing the maintenance of cell viability, even after cell freezing and thawing. Therefore, new lines, limited to the number of replications in vitro, have been established by using embryo tissues from *Ixodes scapularis* (Say), of which line IDE8 is the most widely known. Currently, various other lines, including Argasidae cells, have already been established (MATTILA et al, 2007; BEL-SAKYI et al, 2009).

Between 2001 and 2009, there has been a significant increase in the establishment of new lines, reaching a total of 46 lines established from different species of ticks. The line bank known as The Tick Cell Biobank, located in Pirbright, Surrey (United Kingdom), includes many other cell lines. Some of them had been previously established, but all of them are limited by the number of in vitro replications. Dr. Lesley Bell-Sakyi is responsible for the bank. The address is; http://www.pirbright.ac.uk/research/Tickcell/Default.aspx.

Despite the low efficacy of primary tick cultures for growing pathogens, some success has been reached from the culture of viruses and bacteria from the genus *Rickettsia* (YUNKER, 1971; REHACEK, 1971, 1972). However, after the establishment of the first lines, cell cultures from different organs and tissues of ticks have been effectively used to isolate various microorganisms, such as arbovirus (VARMA et al, 1975; LEAKE et al, 1980; YUNKER et al, 1981); Chlamydia (SHATKIN et al, 1977); protozoa (BHAT et al, 1979), mycoplasmas (TULLY et al, 1981), Borrelia (KURTTI et al, 1993; OBONYO et al, 1999; VARELA et al, 2004), *Ehrlichia* (MUNDERLOH et al, 1996), *Rickettsia* (SIMSER et al, 2001) and *Anaplasma* (BLOUIN et al, 2002). However, autochthonous cell lines are important for the success of specific pathogen cultures.

Generally, bioagents are transmitted by saliva injected to the site of the bite, which, on the other hand, presents toxins, anesthetic and anticoagulant substances, the latter with therapeutic applicability. After the construction of the cDNA library from salivary glands of *A. sculptum* (known as *A. cajennense*, BATISTA et al, 2008), a recombinant protein has been elected, known as Amblyomin-X, showing, besides anticoagulant capacity, also antitumoral action (SIMONS et al, 2011).

With the exception of ticks *R. microplus* and *R. sanguineus*, cells from established lines so far have been obtained from species which are not from the neotropical region. This is why the establishment of simile embryo stem cells from *A. sculptum*[1] and other neotropical species is important, since all of them may potentially be vectors for microorganisms, some of them highly lethal, such as *Rickettsia* from the group of spotted fever.

The species *Amblyomma cajennense* (Fabricius, 1787) forms a complex of species currently comprising 6 axons (BEATI et al, 2013; NAVA et al, 2014). In Brazil, *A. cajennense sensu strictu* is present from the Amazon region to the State of Mato Grosso, while *A. sculptum* is found in the rest of Brazil, North of Argentina, Bolivia and Paraguay.

A few works on the establishment of tick cell lines have already been published, such as: Bhat & Yunker (1977), Establishment and characterization of a diploid cell line from the tick *Dermacentor parumapertus* Neumann (Acarina: Ixodidae); Yunker & Meibos (1979), Continuous cell lines from embryonic tissues of ticks; Bell-Sakyi (1991), Continuous cell lines from the tick *Hyalomma anatolicum anatolicum*. Despite Esteves et al (2008) have analyzed BME26 cells from *R. microplus* as potentially microbicide and autophagic, no paper has so far mentioned the characterization with mesenchymal and cell differentiation markers for the cultures as obtained.

The Brazilian Patent PI 9610681-6, filed on Aug. 23, 1996 and published on Aug. 3, 1999 (corresponding to the international patent application PCT/US1996/013594) in name of REGENTS OF THE UNIVERSITY OF MINNESOTA and OKLAHOMA STATE UNIVERSITY, under the title Processo de cultivar rickéttsias em cultura de células, limitadas pelo numero dos repiques in vitro, de carrapato *Ixodes scapularis* e de preparar antigenos e vacinas de rickéttsias (Process for cultivating *Rickettsia* in a cell culture, limited by the number of in vitro replications, from the tick *Ixodes scapularis*, and preparing *Rickettsia* antigens and vaccines), discloses process for cultivating *Rickettsia* in cell lines of *Ixodes scapularis*. The processes of said patent are responsible for microorganism culture, such as *Anaplasma marginate, Ehrlichia canis* and *Rickettsia rickettsi*. A process disclosed by the document PI 9610681-6 involves the incubation of a *Rickettsia* with a cell culture from the tick *Ixodes scapularis* in a culture medium under reduced oxygen and increased $CO_2$, at a sufficient temperature to detect the growth of *Rickettsia*. The culture medium comprises an adequate medium for the growth of invertebrate cells supplemented with an organic buffer. The process of cell culture of the document PI 9610681-6 may be used for large scale production of products containing *Rickettsia* which are useful in assays for diagnosis and vaccine preparations.

The main difference between the invention and the Patent PI 9610681 is that the latter refers to the culture of *Rickettsia* in cell culture, while the present invention refers to the process of isolation and cultivation which is already standardized, as well as the production of cell lines presenting a well-defined composition and which are characterized, may or not be used for the culture of *Rickettsia* and may also be used for many other purposes, such as kits for diagnosis, etc.

Unlike the proposal of the present invention, and as discussed by the patent PI 9610681, the method established by said patent leads to obtaining various cell cultures which do not present any standard concerning their growth or molecular composition, i.e. they have not been standardized, and cannot evolve to an industrial process.

The initial step of establishment of any cell culture in the patent PI 9610681 requires between 6 and 12 months to produce the first subculture, while, in the present invention, that period is much shorter, taking in average less than two months, when, from that moment, cells show acceleration in their growth (critical mass). Therefore, the conditions of culture as used in the present invention allow for faster and much more efficient cell growth.

Furthermore, in the patent PI 9610681, inventors have not focused on a given embryo age for obtaining cell cultures, and thus had an extremely heterogeneous and hardly controllable cell population, which is a characteristic of a primary cell culture and cannot be considered a continued cell line (*Tissue Culture Association Terminology Committee* in 1990 (Schaeffer, W. I., *In Vitro Cell*. (rev. Biol. 26: 97-101, 1990; *ATCC Cell Biology Catalog*, 2007). The invention establishes a concrete embryo age causing the isolation of cells, which may be called simile "embryo" de facto, since they express their markers, besides having self-renovation (continued line) and differentiation characteristics, which is also confirmed by the examples.

The U.S. Pat. No. 4,447,537, filed on Jan. 22, 1981, granted on May 8, 1984 in name of Conrad E. Yunker and John C. Cory and assigned to THE UNITED STATES OF AMERICA AS REPRESENTED BY THE DEPARTMENT OF HEALTH AND HUMAN SERVICES, under the title: Tick Cell Lines, refers to new continued cell lines from tick embryo tissues (Ixodidae); the use of said cells to replicate selected microorganisms; and the use of replicated microorganisms for disease diagnosis, prophylaxis and control in vertebrate animals for infections caused by said microorganisms.

The U.S. Pat. No. 4,447,537 is different from the invention since, for cell isolation, the inventors have considered the culture medium as critical, which is constituted, in equal parts, by MEM and L-15, with high content of fetal bovine serum (20%). The present invention has shown that only the culture medium L-15 was sufficiently efficient for cell production, also reaching low content of 5% fetal bovine serum, being the ideal medium for cell culture. The invention has also shown that supplementation with 20% SBF is ineffective and toxic as time passes, for the cells obtained by the invention, starting apoptosis after a few days.

In the U.S. Pat. No. 4,447,537, cell culture temperature significantly varies depending on the species, while the present invention has allowed to obtain cells from any species, keeping constant temperature. Furthermore, in said U.S. patent, cells have been isolated within 8 to 12 days after the start of oviposition. The present invention proves that the ideal age was 21 days after the start of oviposition, reaching a larger number of viable cells for adherence. The present invention also shows that eggs that are too young produce an insufficient number of cells, presenting difficulties in adherence and forming lumps on the supernatant, which do not develop themselves.

Cells obtained by the U.S. Pat. No. 4,447,537 are predominantly fibroblastoids, while the present invention focuses on obtaining "epithelial" type cells, which form clusters and express embryo stem cell markers, such as Oct3/4 and Nanog.

In other words, established cell lines from ticks, until now, are not embryo or simile embryo, but rather precursor cells or less differentiated cells which are proliferatively active, derived from simile embryo cells from ticks.

Therefore, the method of isolation of cell lines as developed by the present invention shows clear advantages in comparison with those as found in the state of the art, being a quicker, more efficient and more standardized method. Isolated cells are key cells from which other cell lines may be derived. The cells of the invention stably express ESC markers and other typical markers for stem cells. Those cells predominantly grow in suspension, making them different from other lines as already known in the state of the art. The cells of the invention grow with minimum addition of fetal bovine serum (FBS) or in its lack, Growth in suspension will allow the transference of production from those cells to a bioreactor, which, on the other hand, will allow for quicker transference of that technique to industrial scale.

As we can show, none of the documents of the state of the art teaches or even suggests the use of simile embryo stem cells from ticks (Acari: Ixodidae), which is obtained from embryo eggs e.g. of *A. sculptum*, in microorganism replication. Similarly, the use of embryo stem cells from ticks for the production of vaccines, diagnostic kits for the detection of antibodies and antigens, both human and animals, isolation and characterization of different kinds of simile embryo stem cells, and obtaining clones for use in genotyping, is not mentioned.

SUMMARY OF THE INVENTION

To solve the above mentioned problems, the present invention will provide for significant advantages in the production of embryo stem cell lines from ticks (Acari: Ixodidae), which has unlimited potential for its production in vitro, which have been generally obtained from embryo eggs from ticks. Similarly, the present invention will be useful for employing these cell lines for the replication of microorganisms, offering an improvement in its performance and presenting more favorable cost/benefit ratio.

The invention refers to the process for isolating simile embryo stem cells e.g. from the mass of eggs from the tick *A. sculptum*. These cells are similar to the embryo stem cells of mammals as cultured in vitro. They are highly clonogenic, able to produce multiple clones with similar characteristics. They are kept in vitro, even after multiple passages (in vitro replications) allowing for their expansion. Said cell lines may grow in semi-adherent conditions, in suspension or over microcarriers in a culture medium, and may also be adapted to chemically defined synthetic medium not containing constituents of animal origin. They have the unlimited capacity of in vitro proliferation, allowing for their wide use in laboratory and industrial scale (bioreactor).

Since the pathogen is propagated and harvested in cells, processing parameters for purification, enrichment and packing of the vaccine are similar to current pharmaceutical methods in the egg-based methodology. However, there is no waiting time involved, since a cell line being infected grows in a bioreactor to start the process for vaccine production. Until now, there are no vaccines being licensed using stem cells from ticks.

Additionally, the invention may be very useful for the production of recombinant proteins. Infected tick cells, e, g, with baculovirus or any other virus, may be an eukaryotic system able to perform post-translation modifications which are more complex than other systems (e.g. yeast). They have better intracell and molecular machinery to correctly pack proteins from mammals, and thus may provide the best chance to obtain soluble protein when a protein with animal origin is to be expressed. In comparison with other cell lines, we hope to reduce the higher costs and also the time to obtain a protein (less than two weeks), due to larger proliferation of embryo cells from ticks, and the volume of cells which may be used for that purpose.

The invention also allows the use of embryo stem cells from ticks for the production of diagnostic kits for the detection of antibodies and antigens, both human and animal.

BRIEF DESCRIPTION OF DRAWINGS

The structure and operation of the invention, jointly with its additional advantages, may be better understood by reference to the attached drawings and the disclosure below.

FIG. 1 shows a photomicrograph of primary cultures of *A. sculptum*. A: non-adherent simile embryo stem cells, obtained in TC100 medium. B: non-adherent simile embryo stem cells, obtained in SF-900 medium.

FIG. 2 shows a photomicrograph of primary cultures of *A. sculptum*. A: non-adherent simile embryo stem cells, obtained in TC100 medium. B: non-adherent simile embryo stem cells, obtained in SF-900 medium. A-B: adherent simile embryo stem cells, obtained in L-15B medium.

FIGS. 3 to 6 show photomicrographs of primary cultures of simile embryo stem cells of *A. sculptum*. 3: 12-day old egg mass, 10 μm bar. 4: 15-day old egg mass, 10 μm bar. 5: 18-day old egg mass, 100 μm bar. 6: 21-day old egg mass, 20 μm bar.

FIGS. 7 to 12 show photomicrographs of simile embryo stem cells of *A. sculptum* with different ages. 7: 25-day old cells, 10 μm bar. 8: 30-day old cells, 20 μm bar. 9: 30-day old cells, 20 μm bar. 10: 35-day old cells, 100 μm bar. 11: 25-day old cells, 20 μm bar. 12: 60-day old cells, 20 μm bar.

FIG. 13 shows DNA PCR with 16S primer for *A. sculptum*. Expected measurement: 400 pb. 1-3: negative control. 4: positive control. 5-10: DNA from *A. sculptum* (at that time, referred to as *A. cajennense*).

FIGS. 14 to 16 show photomicrographs of cultures of simile embryo stem cells from *A. sculptum* after thawing. 14: thawed cells after 30 days from first freezing. 15: thawed cells after 35 days from first freezing. 16: thawed cells after 56 days from the second thawing. 10 μm bars.

FIGS. 17-20 show photomicrographs of the line of simile embryo stem cells from *A. sculptum* (IBU/ASE-16) as a substrate for pathogen growth. 17-18; *Rickettsia*, cells infected with *Rickettsia belli* and *R. parkeri*, respectively, 1000 μm bars. 19-20: protozoa, cells infected with *Leishmania infantum chagasi* and *Trypanosome theileri*, respectively, 10 μm bars.

FIGS. 21 to 24 show photomicrographs, obtained in a transmission electron microscope, of cells of *A. sculptum* infected with *Trypanosome theileri*.

FIGS. 25 to 28 show photomicrographs, obtained in a transmission electron microscope, of cells of *A. sculptum* infected with *Leishmania infantum chagasi*.

FIG. 29 shows representative dot plot graphs showing the expression of each stem cell marker in the culture of cells of *A. sculptum*. The results have been obtained by flow cytometer, acquired by the program CellQuestPro and analyzed by the program WinMDI 2.9.

FIG. 30 is a bar graph showing average values for the markers of stem cells expressed by cells of *A. sculptum*. The results have been obtained by a flow cytometer, acquired by the program CellQuestPro and analyzed by the program WINmdi 2.

FIG. 31 is a photomicrograph of cells of *A. sculptum* A, totipotent cells; B, melanocytes; C. neuronal type cells.

FIG. 32 are dot plot graphs showing the expression of each marker. Apoptosis, necrosis, proliferation and checking points for the cell cycle of cells of *A. sculptum*. The results have been obtained by flow cytometer, acquired by the program CellQuestPro and analyzed by the program WinMDI 2.9.

Figure 35:
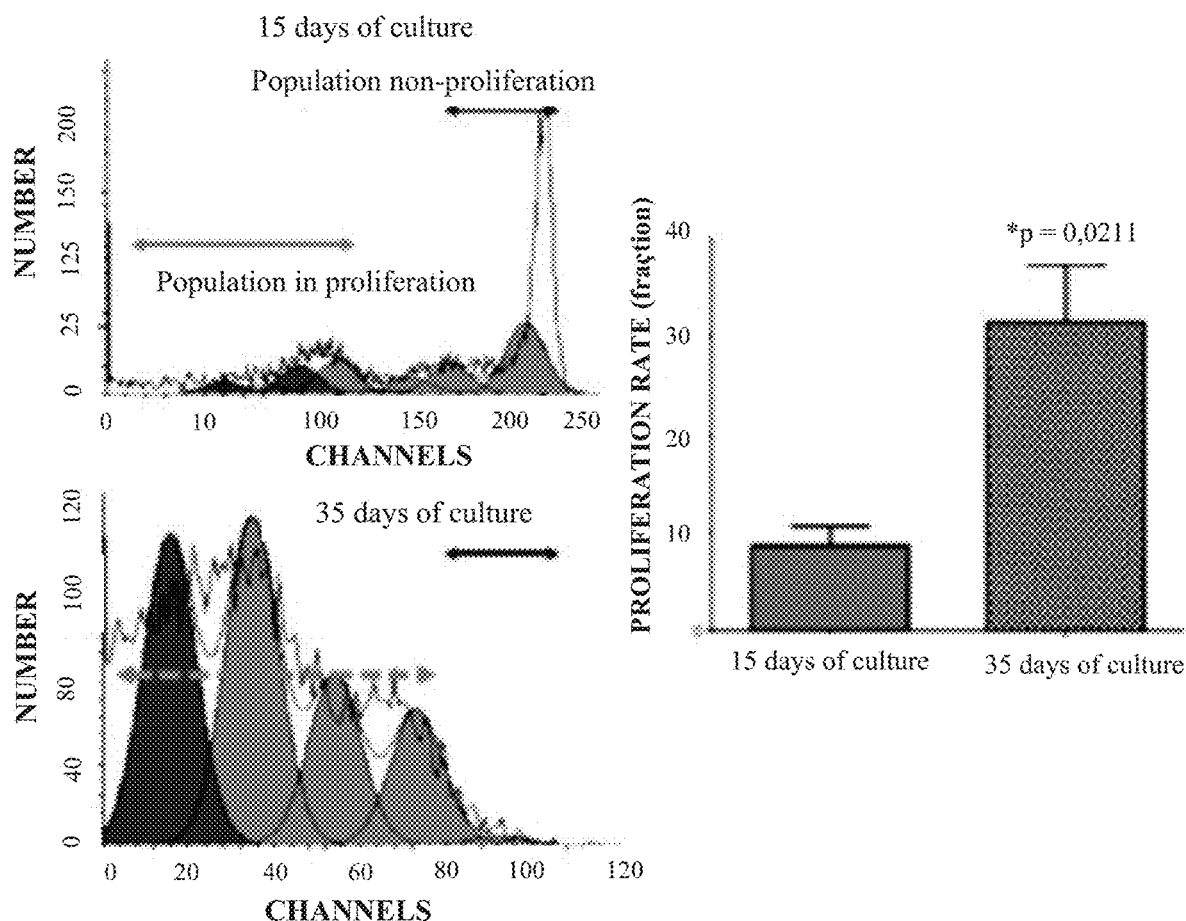

FIG. 35 shows graphs showing the proliferative rate. Average of the studied groups. Reading after 15 days and 35 days of culture.

Figure 36:
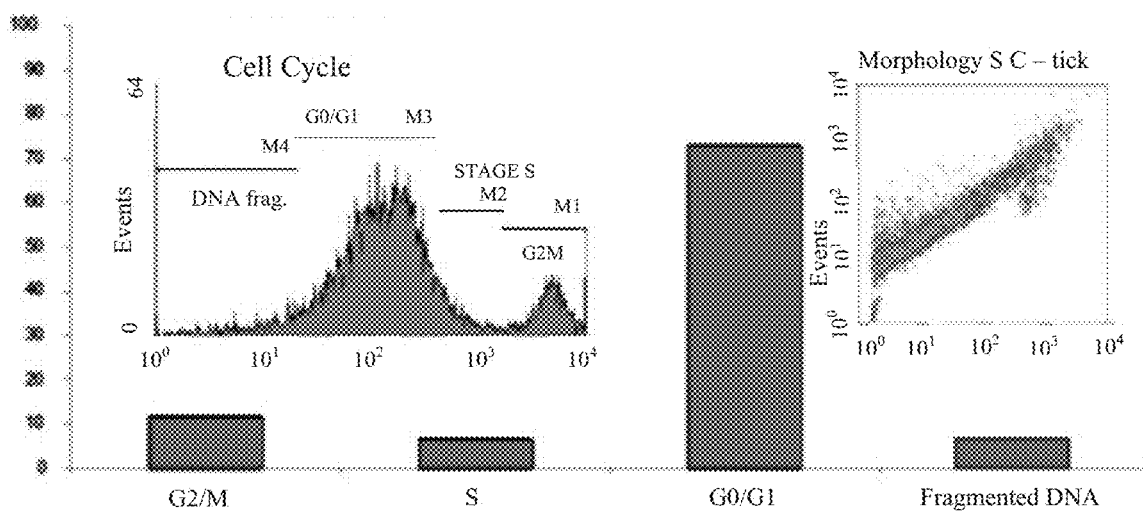

FIG. 36 shows graphs showing different steps of the cell cycle of cells of *A. sculptum* (IBU/ASE-16) 48 hours after subculture.

Figure 37:
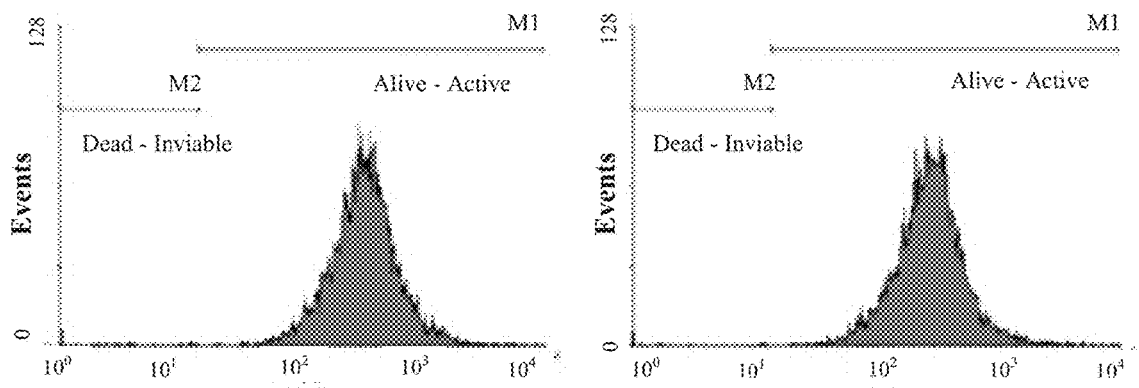

FIG. 37 shows graphs showing the mitochondrial potential of cells (IBU/ASE-16) of *A. sculptum,* 48 hours after subculture.

Figure 38:
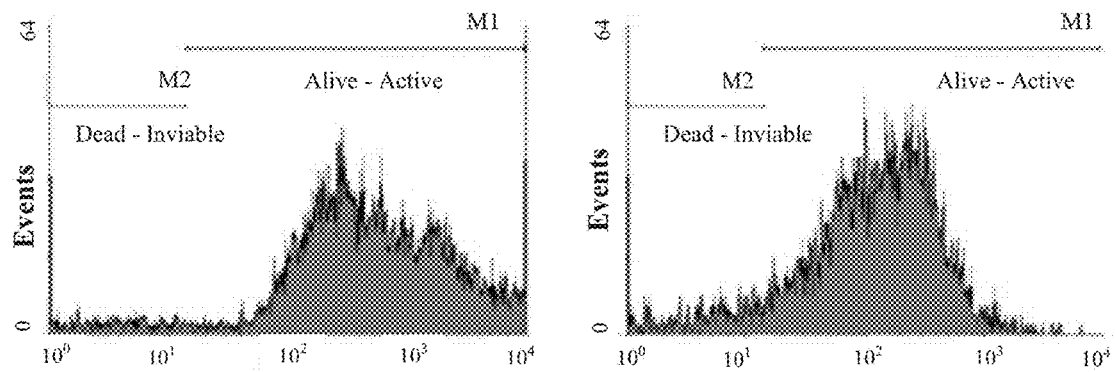

FIG. 38 shows graphs showing the mitochondrial potential of cells (IBU/ASE-16) of *A. sculptum,* 144 hours after subculture.

Figure 39:
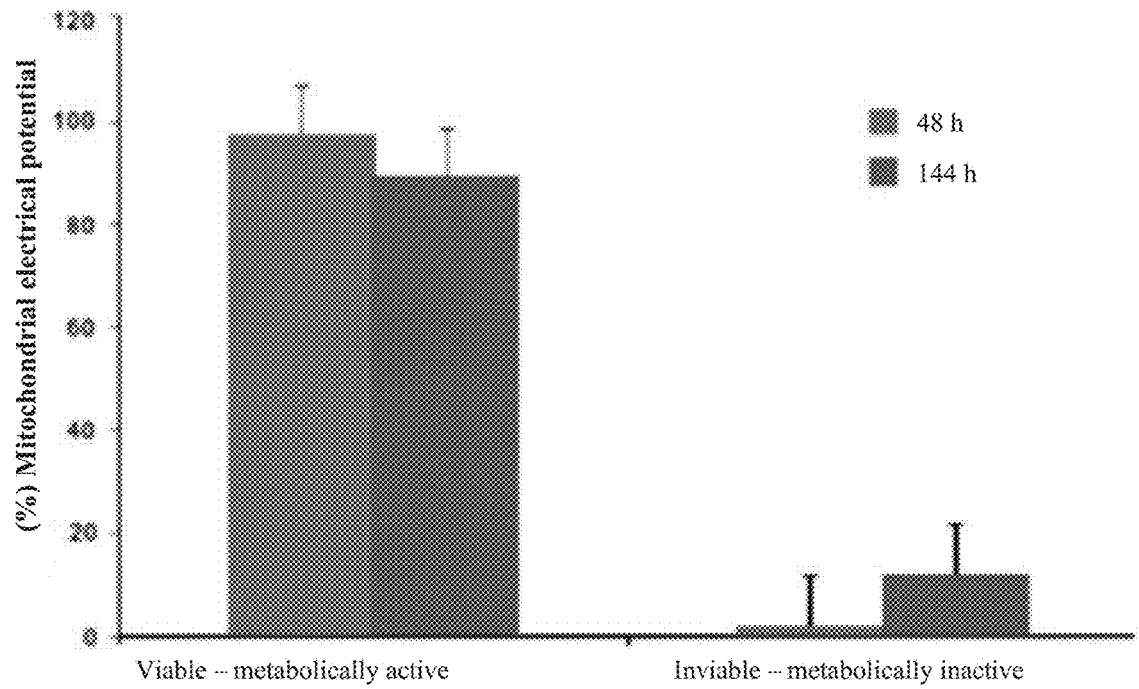

FIG. 39 shows a bar graph representing average values for mitochondrial electric potential of cells of *A. sculptum* as obtained with the probe Rhodamine 123. The results have been obtained by flow cytometer, acquired by the program CellQuestPro and analyzed by the program WINmdi 2.

FIG. 40A-C shows the analysis of the Ndel expression in non-differentiated IBU/ASE-16. In (A1-A2), the expression of Ndel in cytoplasm shows the marking of centrosome (arrow). In (B1-B2), cells are in mitotic division, with chromosomes marked by PI and the centrosome marked by Ndel (arrow). (C1-C2) highlights the marking of Ndel in the cytoplasm of IBU/ASE-16, where the cores are dyed with PI (red). A1, B1 and C1=fluorescence-confocal microscopy, A2, B2 and C2=fluorescence+transmitted (DIC) confocal microscopy. 63× Objective, FIG. 40D-F shows an analysis of Ndel expression in spontaneously differentiated IBU/ASE-16 for neural cells. In (D1-D2), there is expression of Ndel (green) in the cell body and we notice the marking of centrosome (arrow). In (E1-E2), it is possible to notice the marking of Ndel (green) in the axon of differentiated cells for neurons (arrow). In (F1-F2), there is marking of Ndel (green) in the cytoplasm of the differentiated cells for glial cells. Cores are dyed with PI (red). D1, E1 and F1=fluorescence—confocal microscopy, D2, E2 and F2=fluorescence+transmitted (DIC)—confocal microscopy. 20× Objective.

Figure 41:
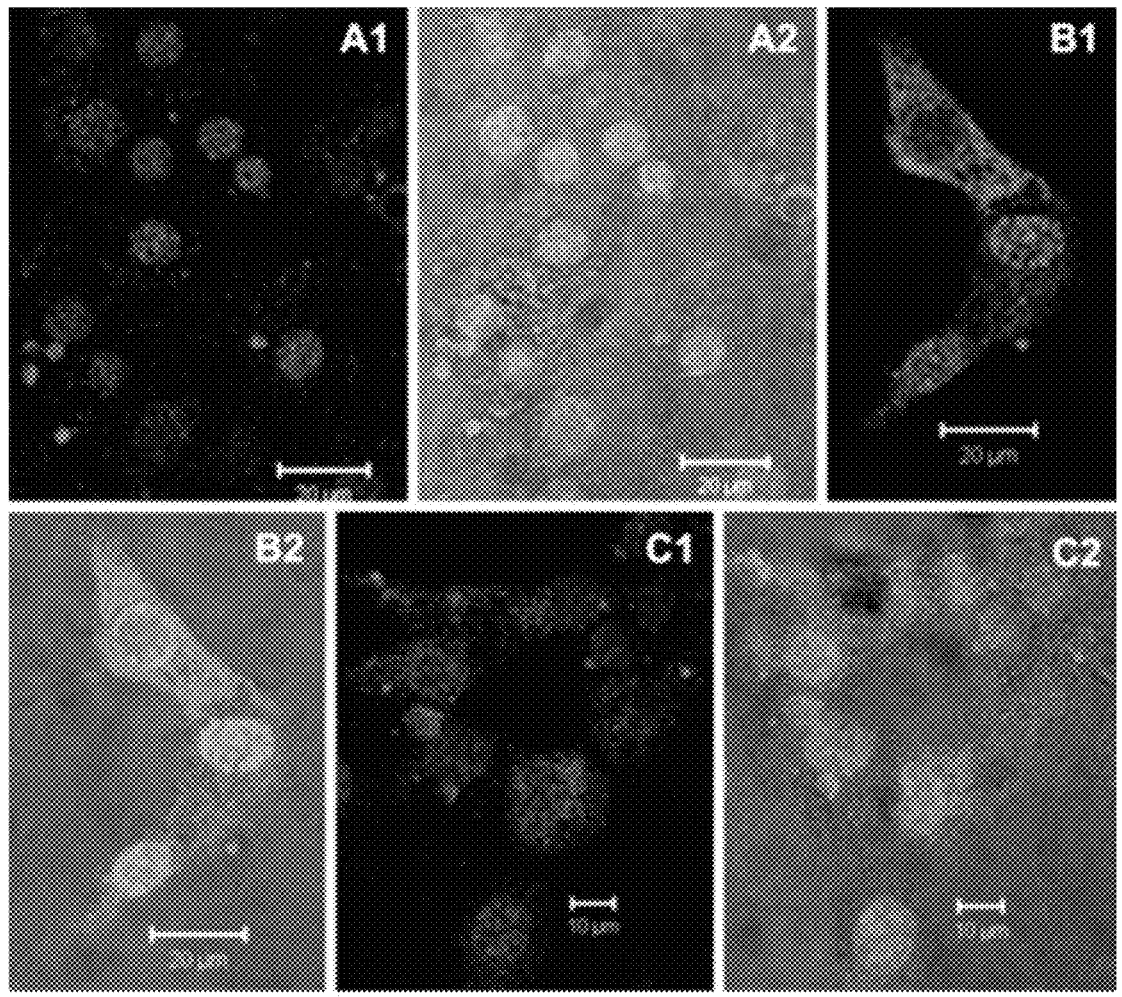

FIG. 41 shows an analysis of ABCG2 expression in non-differentiated IBU/ASE-16. In (A1-A2), ABCG2 expression (green) in the cytoplasm, we can notice point marking. In (B1-B2), it is possible to notice differentiated expression between the cells for the marker ABCG2 (green). In (C1-C2), marking of ABCG2 (green) in the cytoplasm of IBU/ASE-16 colonies. Nuclei dyed with PI (red). A1, B1 and C1=fluorescence—confocal microscopy, A2, B2 and C2=fluorescence+transmitted (DIC)—confocal microscopy. 40× Objective.

Figure 42:
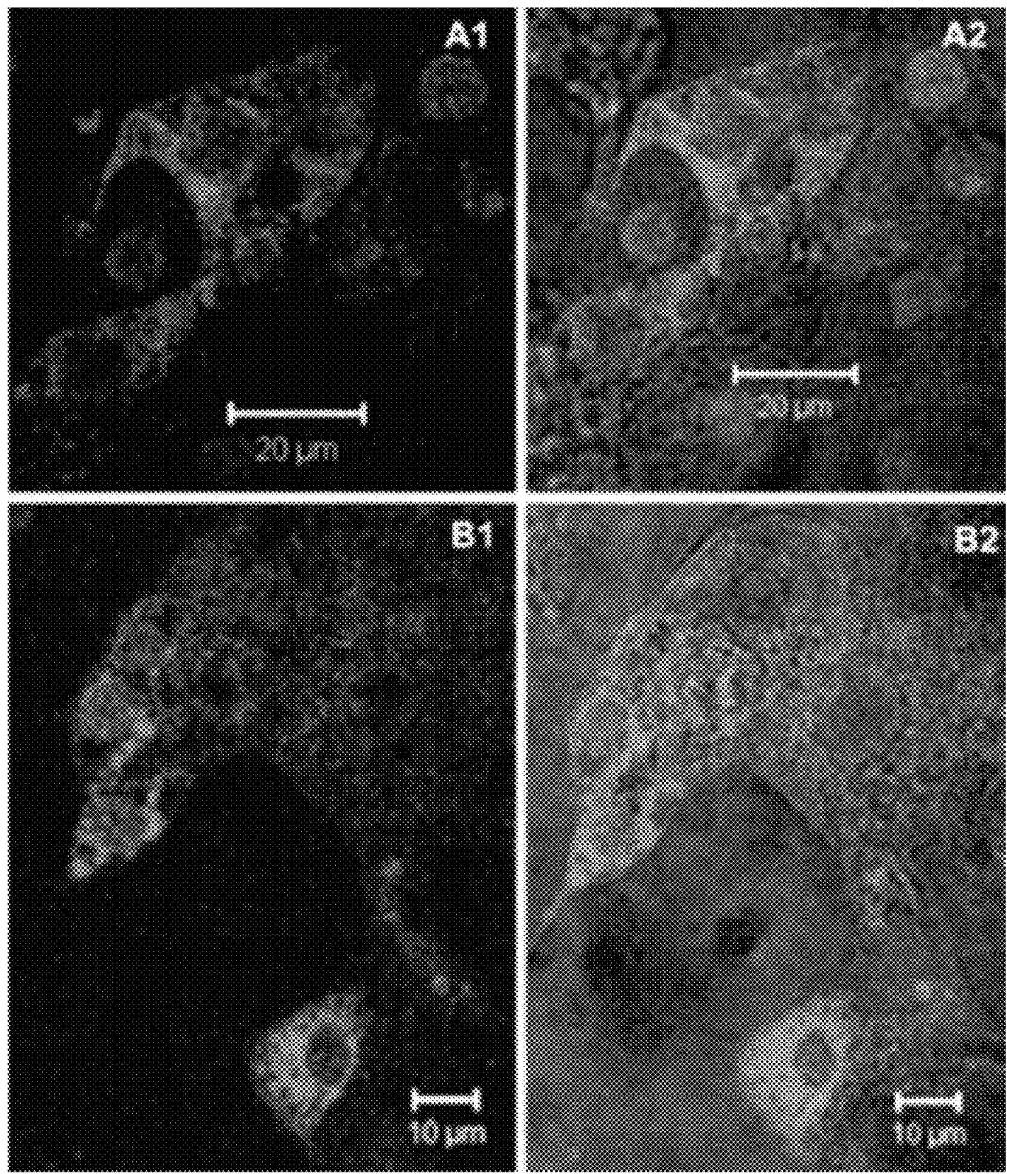

FIG. 42 shows an analysis of CD44 expression in non-differentiated IBU/ASE-16 cell colonies. In (A1-A2), there is expression of CD44 (green) in the cytoplasm and membrane of cells. In (B1-B2), it is possible to notice strong marking of the antibody (green) in cells constituting the colonies. Cores are dyed with PI (red). A1, B1=fluorescence—confocal microscopy, A2, B2=fluorescence+transmitted (DIC)—confocal microscopy. 40× Objective.

Figure 43:
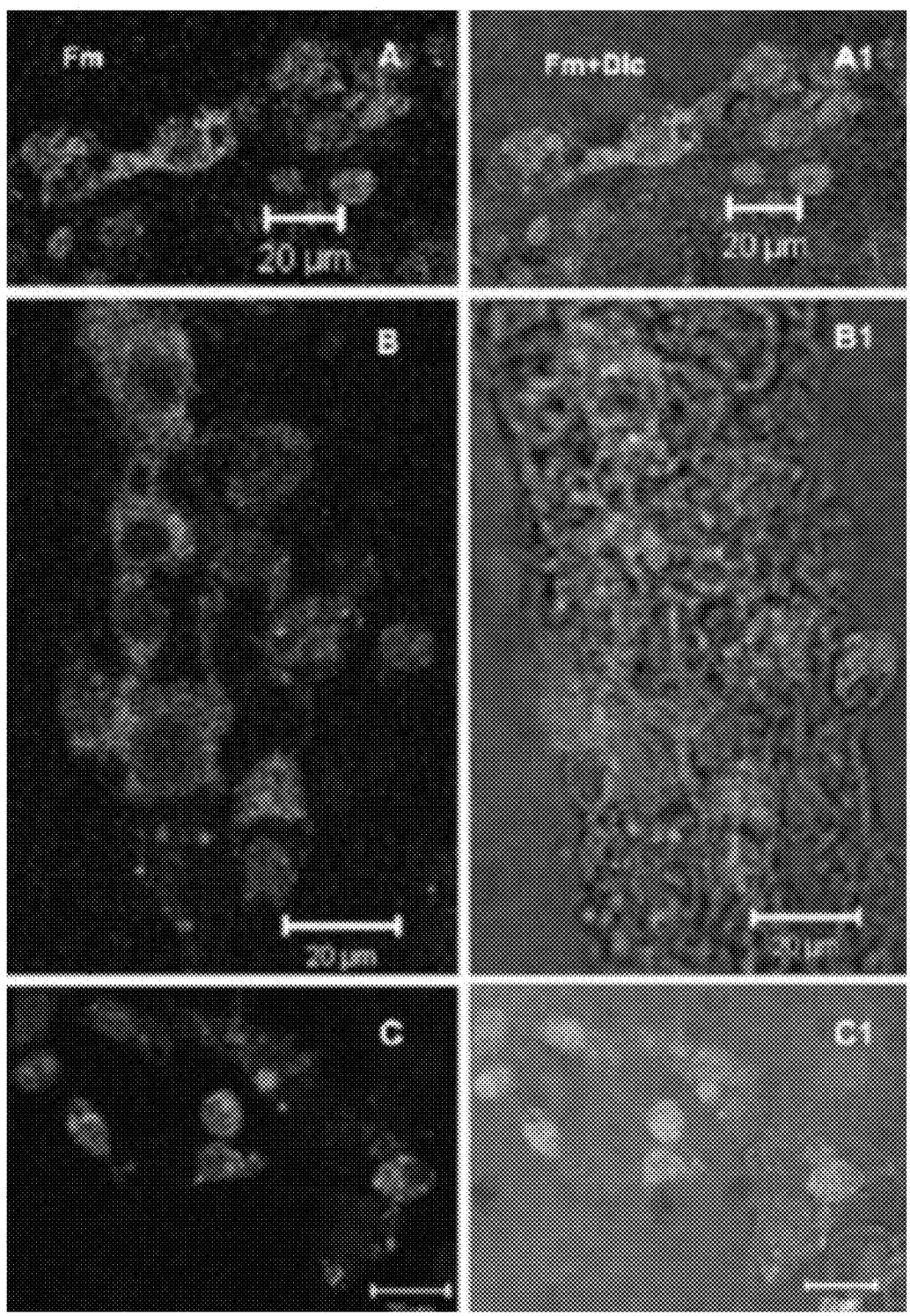

FIG. 43 shows an analysis of Nestin expression in non-differentiated IBU/ASE-16. In (A-A1), there is the expression of Nestin (green) forming cytoskeleton of a few cells. In (B-B1), it is possible to notice strong marking of the antibody (green) in the cells in colonies. In (C-C1), there are individual cells expressing Nestin (green). Cores are dyed with PI (red). A, B, C=fluorescence—confocal microscopy, A1, B1 and C1=fluorescence+transmitted (DIC)—confocal microscopy. A, A1, C and C1=20× Objective; B and B1=40× Objective.

Figure 44:
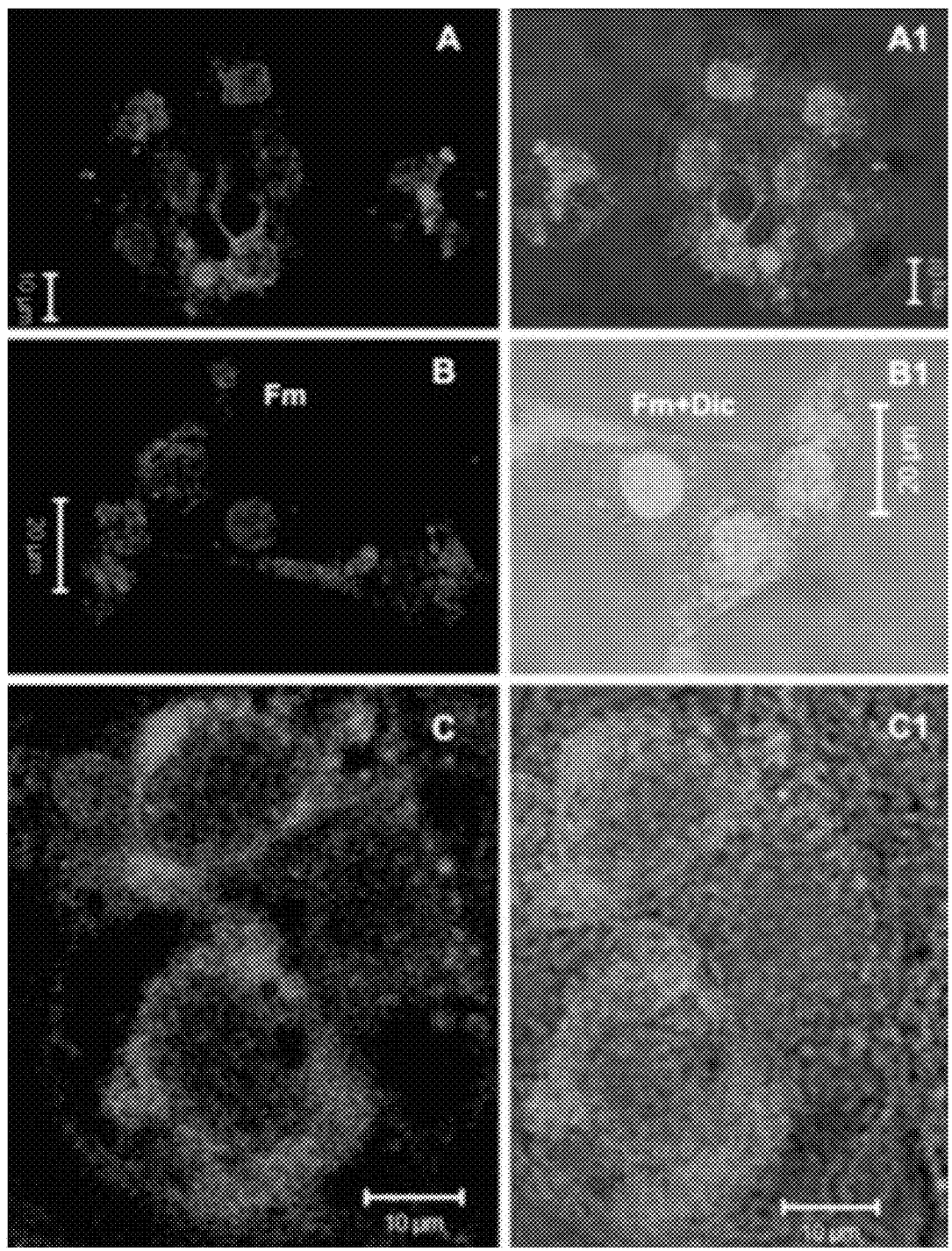

FIG. 44 shows an analysis of the expression of beta-tubulin III on IBU/ASE-16. In (A-A1), there is expression of beta-tubulin III (green) in non-differentiated cells constituting the colonies. In (B-B1), it is possible to notice the marking of beta-tubulin III (green) in spontaneously differentiated cells for neurons. In (C-C1), there is marking of beta-tubulin III (green) in the cytoplasm of non-differentiated cells. Cores are dyed with PI (red). A, B and C=fluorescence—confocal microscopy, A1, B1 and C1=fluorescence+transmitted (DIC)—confocal microscopy. A and A1=10× Objective; B and B1=20× Objective; C and C1=63× Objective.

Figure 45:
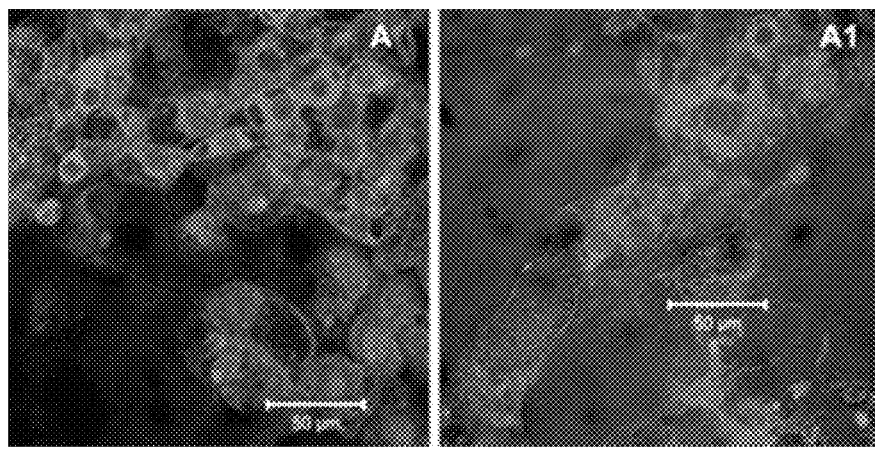

FIG. 45 shows an analysis of alpha-actinin expression in spontaneously differentiated IBU/ASE-16 for muscle cells. In (A-A1), there is the expression of alpha-actinin (green) forming the cytoskeleton of cells, and it is possible to notice the differentiated marking between the cells. Cores are dyed with PI (red). A and A1=fluorescence+transmitted (DIC)—confocal microscopy. A and A1=20× Objective.

Figure 46:
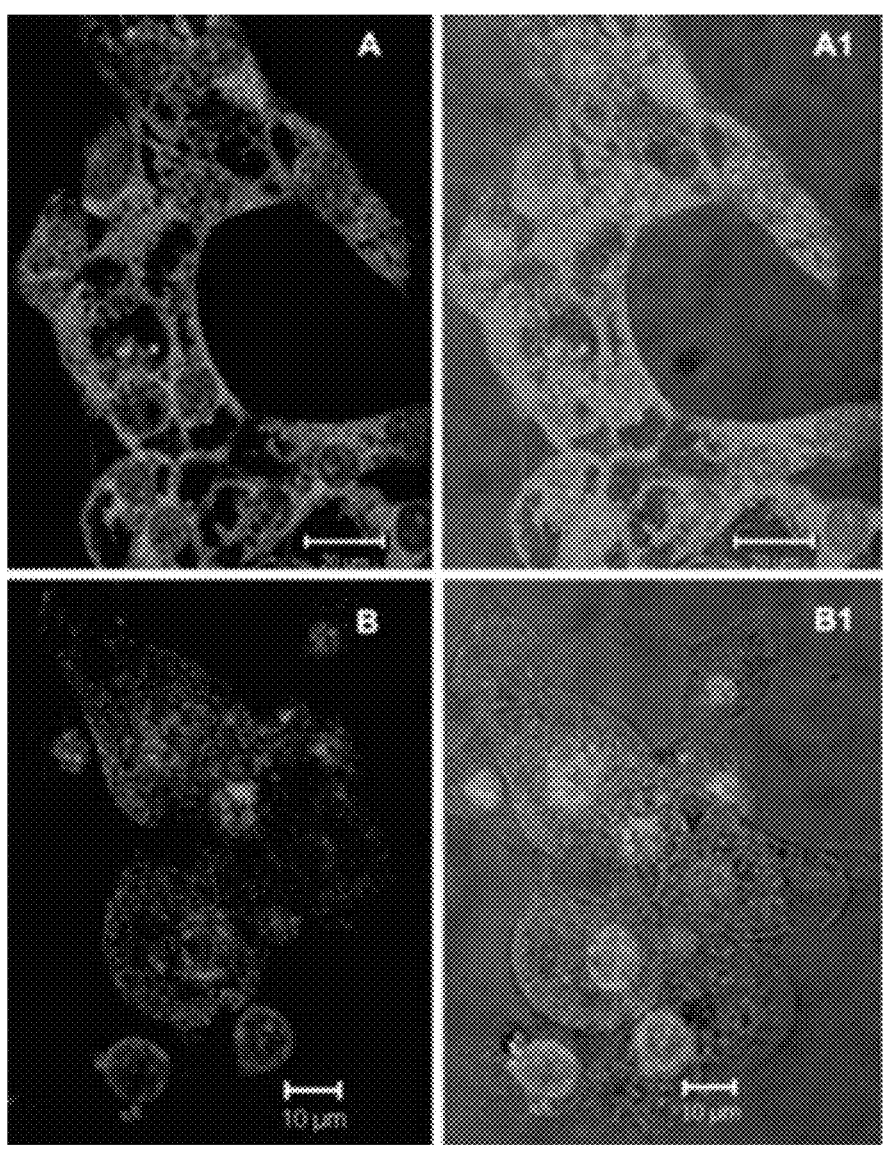

FIG. 46 shows an analysis of expression of Titine in spontaneously differentiated IBU/ASE-16 for muscle cells. In (A-A1), there is the expression of Titin (green) forming the cytoskeleton of cells. In (B-B1), it is possible to notice the differentiated making (green) between the cells. Cores are dyed with PI (red). A and A1=fluorescence+transmitted (DIC)—confocal microscopy. A and A1=20× Objective; B and B1=40× Objective.

Figure 47:
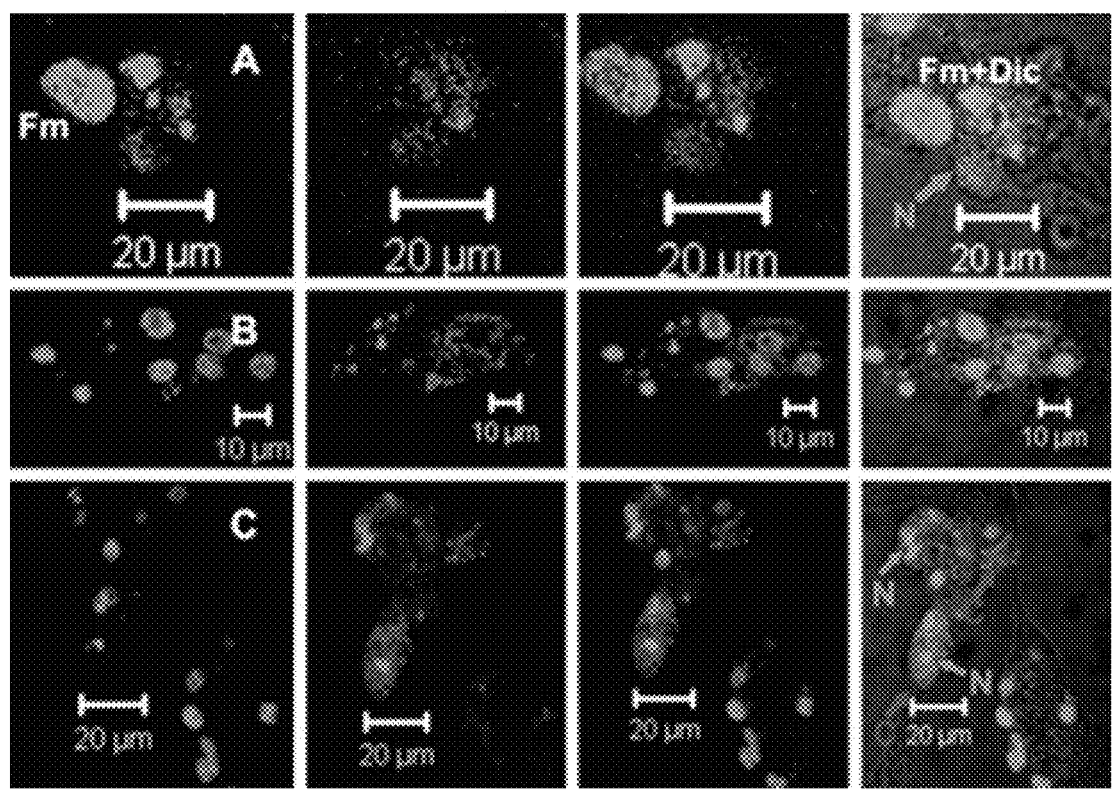

FIG. 47 shows the analysis of Oct-3/4 expression in non-differentiated IBU/ASE-16, In A (row A), there is the expression of Oct-3/4 (green) in the cell core (arrow). In B (row B), there is the expression of Oct-3/4 (green) in the cytoplasm of colony cells. In C (row C), there is the expression of Oct-3/4 (green) in the cell core (arrow) of colony cells. Cores are dyed with PI (red). In yellow, overlapping of the green fluorescence (antibody) and the red fluorescence (core), In the first three columns=fluorescence—confocal microscopy; in the last column=fluorescence+transmitted (DIC)—confocal microscopy. On row A=20× Objective, on rows B and C=10× Objective.

Figure 48:
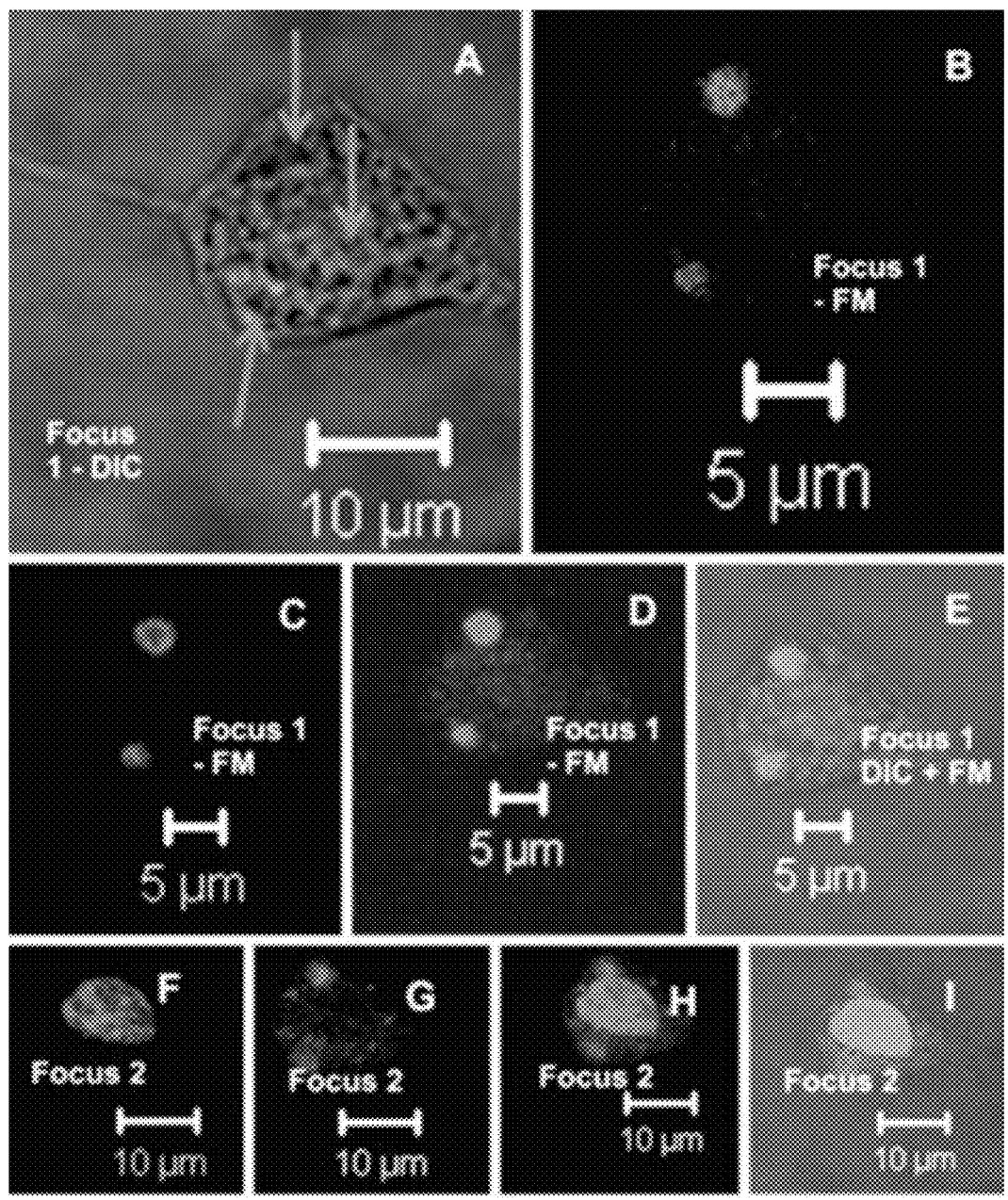

FIG. 48 shows an analysis of Oct-3/4 expression in non-differentiated IBU/ASE-16. In (A) transmitted (DIC) of a three-core cell (arrows). In (B), a two-core cell with cores marked with PI (red), In (C), the expression of Oct-3/4 (green) in the two-core cell. In (D), overlapping of the expression of Oct-3/4 (green) and cores (red) in the two-core cell. In (E), overlapping of the expression of Oct-3/4 (green) and cores (red) in the two-core cell in addition to transmitted (DIC). In (F), a cell with core marked with PI (red). In (G), same cell as (F), but showing the expression of Oct3/4 (green) in cell cytoplasm. In (H), overlap of (F) and (G). In (I), addition of transmitted (DIC) to the image (H). Cores are dyed with PI (red). In yellow, overlapping of the green fluorescence (antibody) and the red fluorescence (core). A, E, I=fluorescence+transmitted (DIC)—confocal microscopy. B, C, D, F, G, H=fluorescence—confocal microscopy. A and B=63× Objective; C, D and E=40× Objective and F, G, H and I=20× Objective.

Figure 49:
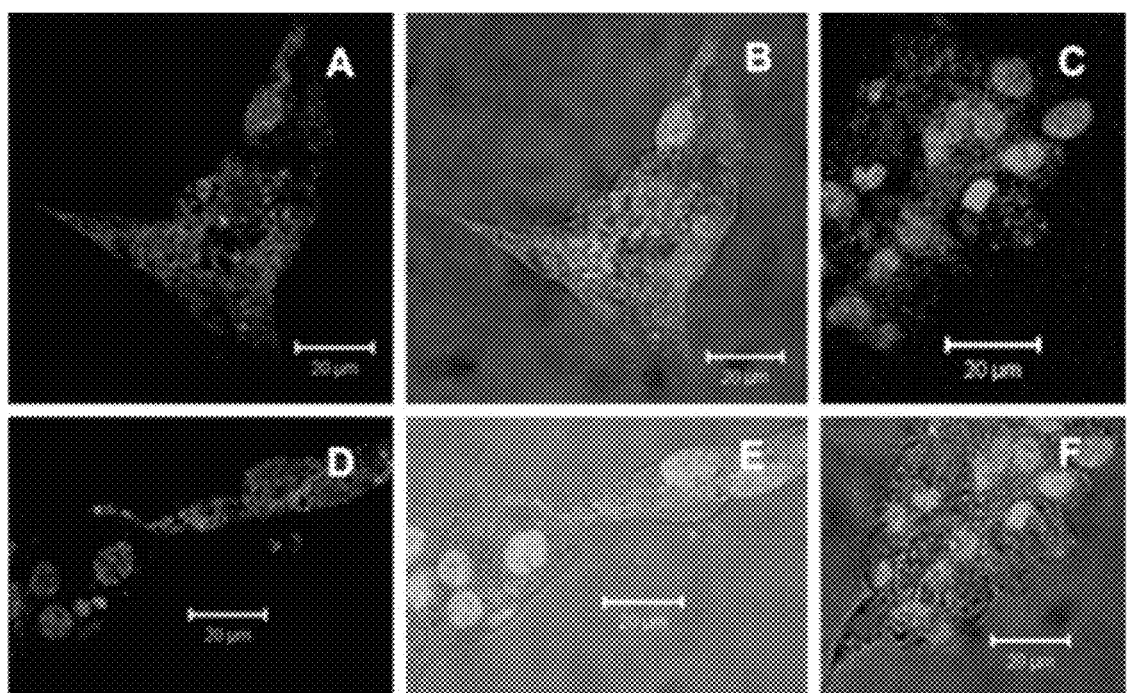

FIG. 49 shows an analysis of the expression of Integrin beta-I in non-differentiated IBU/ASE-16. In (A-B), there is expression of Integrin beta-I (green) in the cytoplasm and the membrane of cells. In (C), it is possible to notice weak marking of the antibody (green) in cells constituting the colony. In (D-E), it is possible to notice the differentiated expression (green) between the cells. In (F), it is possible to notice the differentiated expression (green) between the cells constituting the colony. Cores are dyed with PI (red). A, C, D=fluorescence—confocal microscopy, B, E, F=fluorescence+transmitted (DIC)—confocal microscopy. 20× Objective.

Figure 50:
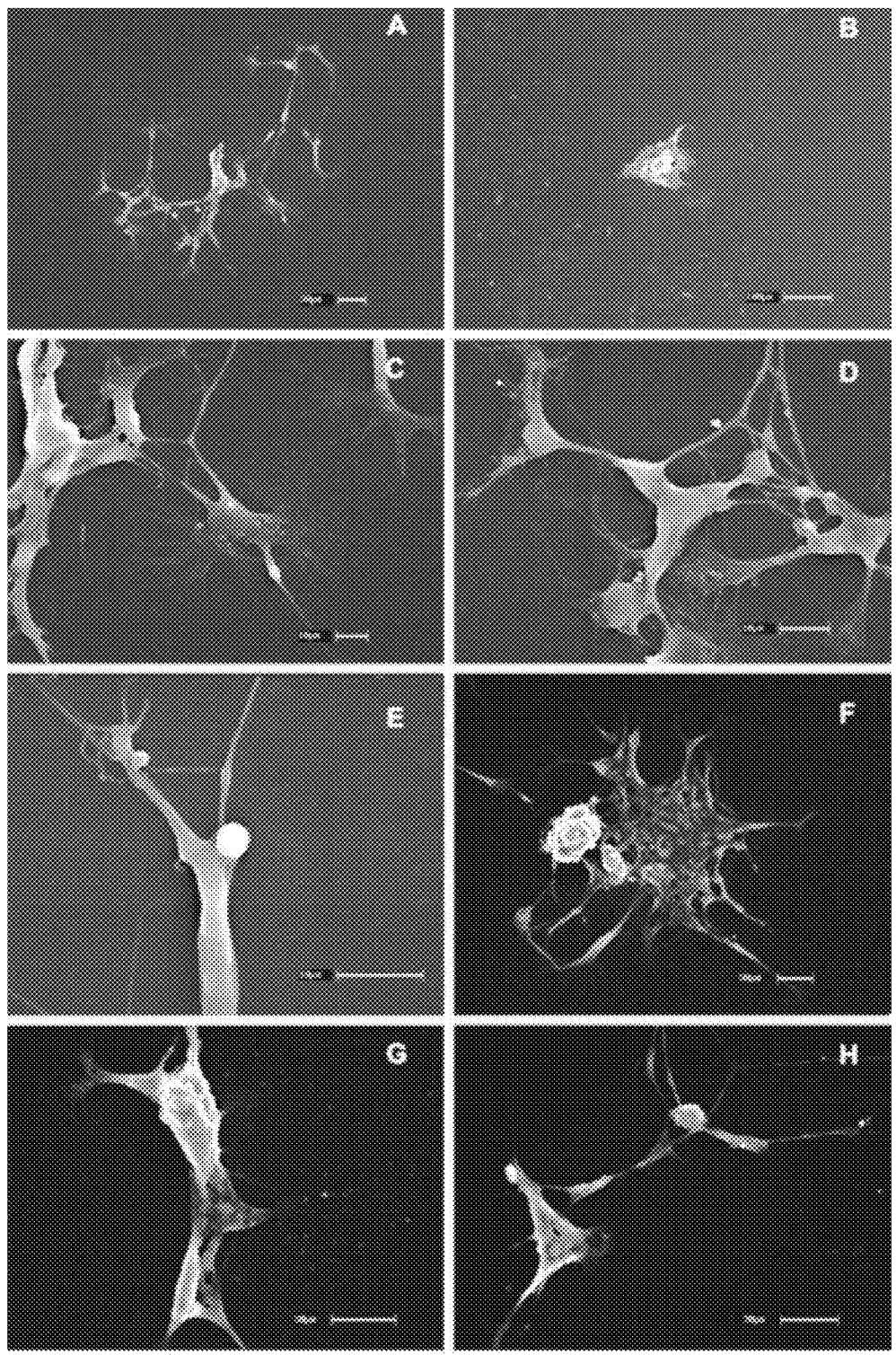

FIG. 50 shows a scanning electron photomicroscopy of simile embryo stem cells of line IBU/ASE-16. A-B, cells in monolayer. C-F, cells in division. G-H, intercellular junctions and connections.

Figure 51:
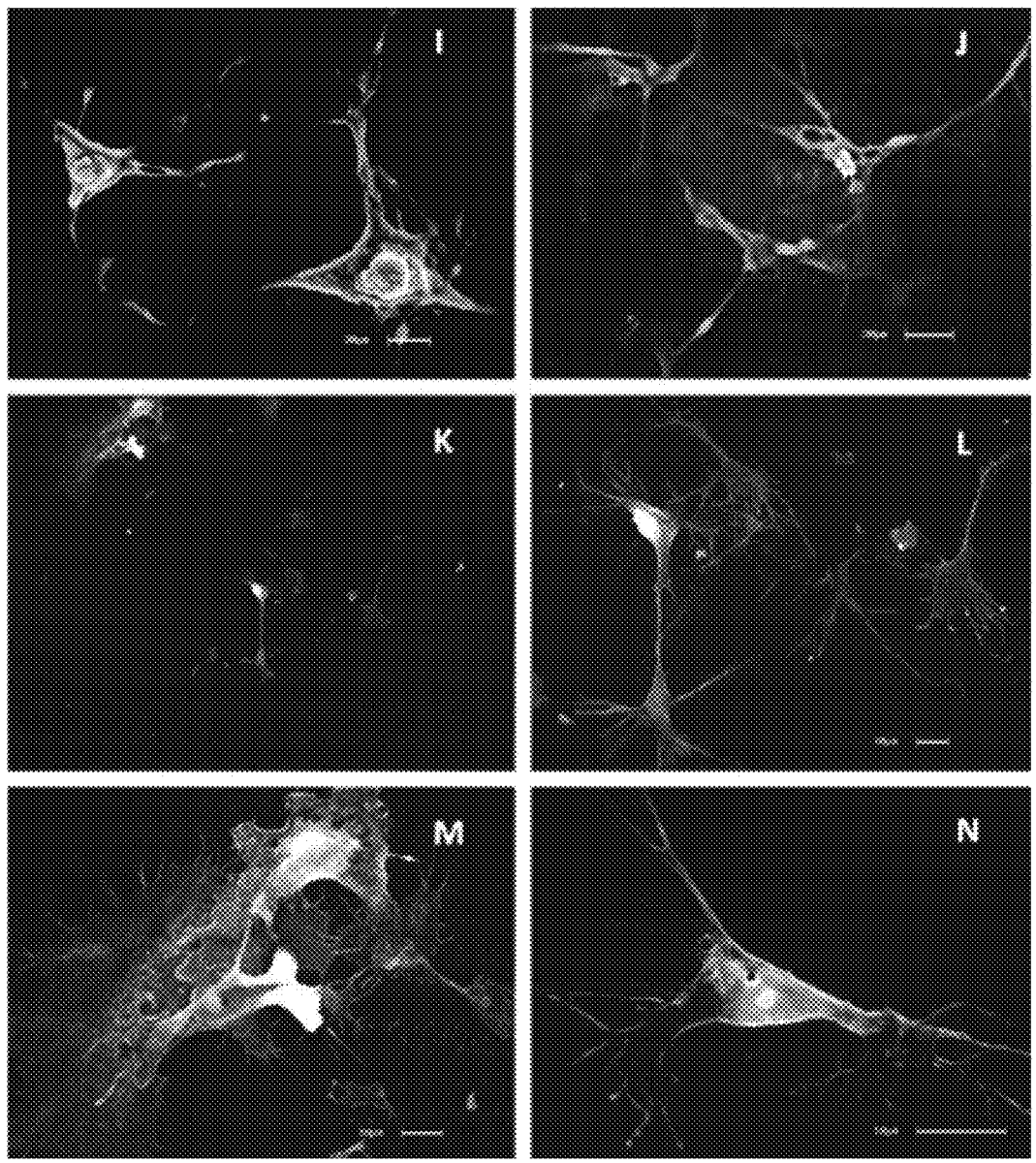

FIG. 51 shows a scanning electron photomicroscopy of simile embryo stem cells of line IBU/ASE-16. I-J, intercellular junctions and connections. K-M-N, formation of extracellular matrix. K-L, formation of neuronal networks.

Figure 52:
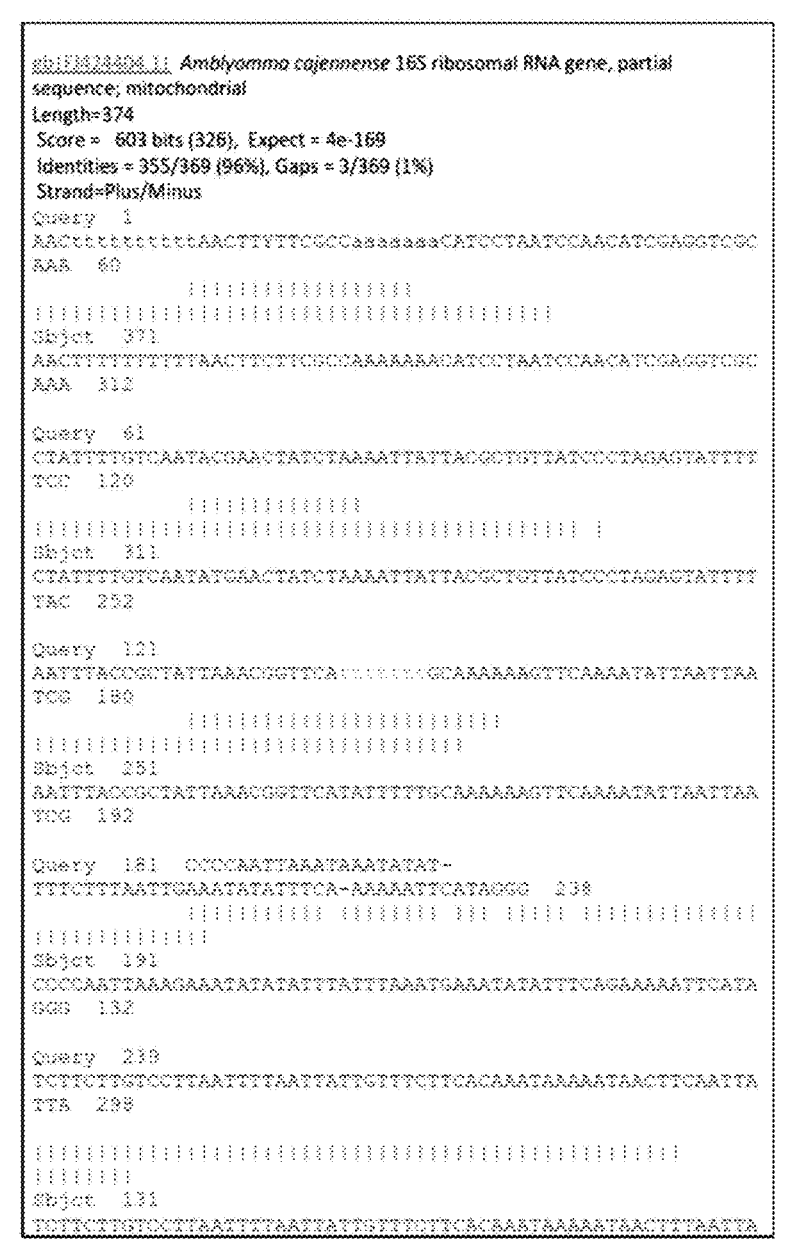

FIG. 52 shows that the sequencing of IBU/ASE-16 (deposited as *A. cajennense*, but corresponding to *A. sculptum*) has shown similarity in comparison with other sequences as already deposited with Genbank, according to the BLAST of the partial sequence of the 16S ribosomal gene).

DETAILED DESCRIPTION OF THE INVENTION

Although the invention may be susceptible to different embodiments, drawings and the detailed discussion below show a preferred embodiment with the understanding that the present embodiment should be considered as an example of the principles of the invention, not intending to limit the invention to what has been shown and disclosed herein.

The invention refers to a process for the production of simile embryo stem cells from ticks, an example given for the species *A. sculptum* (Acari: Ixodidae), which are obtained from embryo eggs. The invention also refers to the use of those embryo stem cell lines for micro-organism replication. More specifically, the invention refers to the use of these embryo stem cell lines for the production of vaccines, diagnostic kits for the detection of antibodies and antigens, both human and animal, isolation and characterization of different kinds of embryo cells and obtaining clones for use in genotyping (biomarkers).

The isolation and characterization of cells of *A. sculptum* with maturing markers and differentiation of mesenchymal and embryo origin, by flow cytometry and confocal laser microscopy, enlarge the knowledge of the main types of cells of the line IBU/ASE-16. The proteomic and metabolomic analysis of IBU/ASE-16 cells and the conditioned medium in the presence of pathogens, is of vital importance in the discovery of biomarkers with pharmaceutic and biotechnological applications. Also, the state of the art extremely lacks works on the characterization of cell lines of ticks.

The deposition of biological material referring to the cell line IBU/ASE-16 was deposited with Collection Nationale de Cultures de Microorganismes (CNCM), located at INSTITUT PASTEUR (25, Rue du Docteur Roux F-75724 Paris Cedex 15) under the access number CNCM I-5000, according to the Budapest Treaty on the International Recognition of Deposit of Microorganisms for the Purposes of Patent Procedure.

DEFINITIONS

Stem cells are non-differentiated cells, i.e. non-specialized cells, which may be defined by two peculiar properties: self-renovation and differentialization potential. Embryo stem cells (ESC) may be generated from the internal cell mass. The pluripotency of ESC is defined based on the following criteria: (i) they form embryoid bodies in vitro; (ii) they can generate teratomas in vivo; and (iii) when injected into a blastocyst, they contribute to all somatic and germen cell lines. The characteristics as previously disclosed are kept by a set of transcription factors and genes as recently defined, including Oct3a/4, Naog, Sox2.

Isolated stem cells from tick eggs, even presenting various properties of ESC, cannot be referred to as being ESC. This is because they present characteristics which cannot be verified, e.g. being injected into a blastocyst. Therefore, we define these cells as simile ESC, since they express said markers as Oct3/4 and Nanog, as well as other markers for stem cells. We also show the ability of those cells to become differentiated in vitro in various types of cells derived from the three embryo leaflets: mesoderm, ectoderm, endoderm.

Obtaining Egg Masses:

Females of *A. sculptum* fully engorged with New Zealand rabbits (*Oryctolagus cuniculus*) were washed with tap water, distilled water, 70% alcohol and 1-3% hypochlorite. They were subsequently immersed in a 1-3% solution of benzalkonium chloride for 5-10 minutes and in sterilized distilled water containing antibiotics for five minutes. After dried in sterilized gauze, they were individually plated on sterile Petri plates nd kept in a biological oven with oxygen demand (BOD) at 27° C. and 80-85% humidity to perform oviposition.

Analysis of Different Culture Media:

Considering that culture media significantly interfere with cell growth, cultures were performed in different media (Leibovitz L-15, TC-100 and SF-900) for *A. sculptum*. Different concentrations of supplements for enriching culture media—broth of Triptose Phosphate and Fetal Bovine Serum—have been used (2%, 5%, 10% and 5%, 10%, 20%), respectively. Cultures were distributed on six-cavity culture plates and maintained in an oven at 28-34° C. for a week.

Therefore, full L-15B medium supplemented with 5-10% fetal bovine serum (FBS) was used for cell cultures, since it is more adequate for the growth of cells of *A. sculptum*. The composition of the used medium follows below:

L-15 with sugars and amino acids, antibiotics and antimycotic
L-Glutamine
Broth of triptose phosphate
Lipoprotein

*Stock Solution D
Vitamin solution
Fetal bovine serum
*Stock Solution D (Stock A+Stock B+Stock C+Stock D) was detailed by Munderloh & Kurtti (1989). In summary, it comprises: A—CoCl+6H$_2$O, CuSO$_4$+5H$_2$O, MnSO$_4$+H$_2$O, ZnSO4+7H$_2$O; B—NaMoO$_4$+2H$_2$O; C—Na$_2$+SeO$_3$; D—reduce glutathione+Stock A+Stock B+Stock C.

Primary cultures and evaluation of the ideal age of eggs of A. sculptum:

The following ages of the egg masses laid by females have been evaluated: 12, 15, 18 and 21 days. The egg masses, weighing 130 and 200 mg each, were disinfected in benzalkonium chloride, filtered 70% alcohol, antibiotic and antifungic solution, sodium hypochlorite and autoclaved water.

Eggs were broken in full L-15B medium supplemented with SFB. The cell suspension was centrifuged at 100 g for 5-8 minutes. The pellet was re-suspended in the full medium supplemented and added with antibiotics (with 4 µl penicillin/streptomycin and 0.8 µl Amphotericin B). The flasks with culture (25 cm) were then incubated at 28-34° C. in a culture oven. Cells were counted in a Neubauer chamber and cultures were observed daily, in an inverted optical microscope, exchanging the medium weekly. Therefore, a continued line of simile embryo cells of A. sculptum was established and denominated IBU/ASE-16.

Culture Maintenance:

Subcultures of IBU/ASE-16 were prepared according to cell growth and, at each passage, the quantity of antibiotics used was reduced until its complete elimination. When the cell culture reached about 90% confluence, they were taken out from the flask with the help of a cell scraper or by thoroughly washing with a pipette. Subsequently, the cells were centrifuged in a Falcon tube with 6 ml of full medium. The supernatant was discharged and the pellet was re-suspended in 8 ml of medium, which was divided in two flasks, thus performing cell expansion. When a considerable number of replications was reached, after about four passages, the cells started to be cryopreserved.

Cryopreservation and Recovery of Cultures:

An aliquot of the cell suspension of IBU/ASE-16 (dyed with Tripan Blue) was used for cell counting in a Neubauer chamber to calculate the concentration of cells/ml to be used in the cryopreservation process.

The suspension was centrifuged at 100 g for 8 minutes, the supernatant was discharged and the pellet was re-suspended in a culture medium containing 20% Fetal Bovine Serum (FBS) and 10% dimethyl sulfoxide (DMSO), being then distributed in cryopreservation tubes. Cryotubes were kept for four hours at 4° C. in a freezing case known as "freezing container", and then remained for 24 hours in a freezer at −80° C., being subsequently transported to liquid nitrogen drums.

To recover cryopreserved cells, cryotubes were quickly thawed in a water bath at 37° C. The contents were transferred to 15 ml Falcon tubes containing 5 ml culture medium with 10% fetal serum.

After centrifugation (100 g for 8 minutes), the supernatant was discharged and the pellet was re-suspended in 4 ml medium, being incubated in a 25 cm$^2$ flask at 28-32° C.

Analysis of the Gene Profile:

IBU/ASE-16 identity was confirmed by means of Polymerase Chain Reaction (PCR) and gene sequencing. DNA was isolated using Puregene DNA Purification System (Gentry Systems, Minneapolis, Minn.) and re-suspended in Milli-Q water. PCR was performed with a 50 µl volume using 1.25 U Taq DNA polymerase, 10× buffer, 0.2 mM dNTP mix, 1.5 mM MgCl, 0.25 mM primers and 1 µl buffer. The thermocycler was scheduled as follows:

Initial temperature—95° C. for 5 minutes (denaturation step), 10 cycles at 92° C. (1 min), 48° C. (1 min), 72° C. (1.5 min), 32 cycles at 92° C. (1 min), 54° C. (35 s), 72° C. (1.5 min) and final extension at 72° C. for 7 minutes. After confirming the sample was positive by PCR, the amplified material was purified by using a QIAquick PCR Purification Kit. The material was sequenced and DNA fragment sequences of the cells were analyzed by Blast. The sequences were similar to those of A. cajennense deposited at GenBank, but in fact corresponding to A. sculptum, since, until end 2013, species from the complex A. cajennense were not yet separated (BEATI et al, 2013; NAVA et al, 2014).

Efficiency of Cell Culture as a Substrate for Cultivating Microorganisms:

Genus Borrelia:

Samples of blood from suspected patients, collected in EDTA (ethylene diamine tetra-acetic acid, disodium salt), were provided by the simile Lyme Disease Laboratory of the Rheumatology course of the School of Medicine of the University of Sao Paulo. Blood from those patients was inoculated in primary cultures of IBU/ASE-16 and those cultures were kept under the same conditions as already disclosed. Besides blood, ticks which were artificially fed with blood from suspected patients were also tested.

The species B. burgdorferi (strain 39/40) was equally tested, being inoculated in IBU/ASE-16 cultures under concentration of approximately 40,000/ml.

Rikettsia and Protozoa:

1 ml portions of Rickettsia bellii and R. parkeri were inoculated in primary cultures of IBU/ASE-16. After slowly shaking for 1 hour, cultures containing L-15B+SFB 5%+Rikettsia were kept at 28° C.

At each three days, the cultures were evaluated to measure the level of infection, by means of Gimenez dyeing. For that purpose, monolayers of cells showing infection close to 100% were scraped and the cell suspension was centrifuged. The sediment was re-suspended in a sucrose-phosphate-glutamate (SPG) buffer, pH 7.0, sterile and frozen at −80° C.

Two species of Trypanosomatidae, Trypanosoma (Megatrypanum) theileri and Leishmania infantum chagasi, originated from axenic cultures, kept in LIT (Liver Infusion Tryptose) medium and added with 10% SFB, were used to evaluate infection in IBU/ASE-16 cultures. For that purpose, portions of 10$^9$ parasites from each species (epimastigotes and promastigotes, respectively) were inoculated in the IBU/ASE-16 cultures. These were incubated at the temperature of 30° C. Infection on the cell monolayer was followed for 30 days.

Isolation of IBU/ASE-16 Clones and Subclones with Markers:

Cells were removed from flasks by using a cell scraper. Once isolated, they were prepared on plates containing markers. Some markers were used both for flow cytometry and for confocal microscopy.

Cell Characterization by Flow Cytometry:

The analysis were performed in the flow cytometer Becton Dickinson FACScalibur (Becton Dickinson, San Jose Calif., USA). That cytometer allows to analyze up to four independent markings in the sample. Power characteristics from each laser, detector and compensation voltage between various lasers—so that a sample of non-marked cells does not allow the presence of positive events for any kind of fluorescence—were previously defined by the use of negative and positive controls for each used fluorochrome. Then, marked and non-marked samples with specific antibodies confirmed the positive events for fluorescence as expected for each tested sample.

IBU/ASE-16, in the sixth culture passage, were taken out from the flask with 1 ml FACS buffer and centrifuged at 800 g for 10 minutes. The pellet was re-suspended and transferred to six tubes, containing 1 ml of cell suspension each, adding other substances as follows:

Tube 1: RNAse alcohol—2 ml;
Tube 2: RNAse alcohol—2 ml;
Tube 3: Markers—4% Paraformaldehyde, pH 7—2 ml;
Tube 4: Markers—4% Paraformaldehyde, pH 7—2 ml;
Tube 5: Mitochondria—4% Paraformaldehyde, pH 7—2 ml; and
Tube 6: Mitochondria—4% Paraformaldehyde, pH 7—2 ml.

The tubes were sealed with parafilm, slowly inverted three times and kept at −20° C. The whole procedure was performed on ice. For the characterization of IBU/ASE-16, the following markers were used, divided into:

stem cell markers: OCT3/4, Nanog, STRO1, CD105, CD90, CD34, CD117, CD133 and VEGF-R1;

proliferation markers, regulators of the cell cycle and death progression: Caspase-3, Ki67, Bcl-2, Cyclin D1 and p53.

CD34 (R&D Systems): this is an adherence molecule, sialomucine, expressed in endothelial cells and hematopoietic parent cells. It may be expressed in some kinds of tumor, indicating angiogenesis potential (BRUCE et al, 2009).

CD117 (Santa Cruz): or c-Kit is a tyrosine kinase marker expressed in hematopoietic stem cells, myeloid parents and gastrointestinal tumors (SARLOMO-RIKALA et al, 1998).

CD133 (Santa Cruz): it is a transmembrane protein, expressed in hematopoietic stem, glial, bone marrow and endothelial parent cells (SHMELKOV et al, 2008).

VEGF-R1 (Santa Cruz): or a vascular endothelial growth factor is a homodimeric protein, involved in tumor angiogenesis and metastasis. It also stimulates recruiting of stem cells (KAYA et al, 2002; ERIKSSON & ALITALO, 2002).

CD105 (Santa Cruz): is a membrane glycoprotein expressed on the surface of endothelial cells, activated macrophages, fibroblasts and muscle-skeleton cells (SANZ-RODRIGUES et al., 2004).

STRO-1 (Santa Cruz): it is the best known marker for mesenchymal stem cells (MSC).

CD90 (R&D Systems): it has shown interaction with integrin, tyrosine kinases, growth factors and cytokines, promoting cell events such as adherence, apoptosis, proliferation and migration. Usually, CD90 is used as a marker for MSCs, despite being also expressed in cells such as neurons, endothelial cells, T cells and other immune and non-immune types of cells (BARKER & HAGOOD, 2009).

Recently, CD90 has been used as a marker for pluripotent parent cells, such as bone marrow, synovial tissue, amnion, fat and others (MAFI et al, 2011).

OCT3/4 and Nanog (Santa Cruz): prevailing in embryo and germinative stem cells, these are transcription factors involved in the regulation of gene suppression, causing differentiation and maintenance of pluripotency (SICLAR & QIN, 2010).

To determine the ratio of dead cells per apoptosis or necrosis and cell proliferation by flow cytometry, the following markers were analyzed:

PI—propidium iodide: is a fluorochrome stoichiometrically interspersed to DNA double strands, Fluorescence was collected at FL-2 and is proportional to the DNA content in the cell. In 2n cells found in stages G0/G1 and G2/M of the cell cycle, signal emission is less intense than in S stage cells. Cells located at the hipodiploid peak (Sub-G1) have DNA content lower than 2n and may represent an increase in the occurrence of cell debris and fragmented DNA, which are characteristic events of cell death.

IBU/ASE-16 samples, as previously fixed, were centrifuged at 1000 g for five minutes. The supernatant was discharged, the cells were re-suspended in 1 ml cytometry buffer and centrifuged again. After centrifugation, the supernatant was discharged and the cells were re-suspended in a PI solution, prepared from 5 ml PBS, to which 5 µl Triton 100 (0.01% v/v), 50 µl RNAse A (2 mg/ml) and 20 µl propidium iodide (5 mg/ml) were added. Subsequently, data was obtained from a Flow Cytometer FACSCalibur in 10,000 events and, for analysis, the program Win Mdi 2.8 was used.

Annexin V (Assay Designs): is intended to detect apoptosis in various cell types, by dosing phosphatidylserine (PS). PS is predominantly observed on the internal surface of the lipid bilayer, turned to cytosol. In the cells starting apoptosis, when the cell membrane still remains untouched but suffers disorganization, PS is translocated to the external surface of the bilayer. The appearance of PS on the cell surface is recognized by phagocytes, which receive that signal and remove the cell signaling its "suicide" to the environment. Annexin V is a protein linked to phospholipids having high affinity to PS in the presence of ions of calcium. Changes in that asymmetry of the membrane, which is analyzed by measuring the adherence between Annexin V and the cell membrane, may be detected before morphological changes as related to the start of apoptosis and before the loss of integrity of the membrane. When conjugating Annexin V to FITC (fluorescein isothiocyanate), it is possible to identify and measure the quantity of apoptotic cells in flow cytometry.

Phosphorylated caspase-3 FITC (Santa Cruz): enforcer cysteine-protease aspartate; it signals for apoptosis to occur. It cleaves substrates, causing condensation and core fragmentation, externalization of membrane phospholipids, which will signal for those cells to be phagocyted by macrophages. It indicates cell death by apoptosis (GRIVI-CICHI et al, 2007).

Ki-67 (Dako—clone DM1): core antigen expressed in all stages of the cell cycle, except for G0 (PEÑA et al, 1998).

Cyclin-D1 (Santa Cruz): regulating protein for CDKs (cyclin dependent kinases), involved in the stage G1/S. Amplification or increase in expression changes the cell cycle progression (COQUERET, 2003).

p53 (Santa Cruz): it acts inhibiting the progression of the cell cycle in the G1/S transition, in the presence of damage to the DNA molecule (TRIEB; KOTZ, 2001).

Anti-apoptotic BCl-2 (Dako): it is a repressive protein for death by apoptosis, with active participation in apoptosis regulation, for preventing cytochrome c release. Bcl-2 expression is able to inhibit the generation of reactive species from oxygen and intracellular acidification, also stabilizing the mitochondria membrane potential. Homeostasis is kept by the control of the quantity of anti-apoptotic and pro-apoptotic proteins. Stimuli, such as damage to DNA, cause an increase in the expression of pro-apoptotic proteins. Bcl-2 (anti-apoptotic) is overexpressed in colorectal carcinomas and adenomas. The number and proportion of IBU/ASE-16 line cells, in apoptosis or necrosis, were identified by a phosphatidylserine externalization assay, by means of flow cytometry techniques as proposed by Bucchieri et al (2002). After fully counting cells in a Neubauer chamber, the number of cells was adjusted to a final concentration of $2\times10^5$ cells/100 µl. Subsequently, Annexin V solution added with FITC (fluorescein isothiocyanate) under the concentration of 1 µg diluted antibody in a binding buffer (10 mM Hepes/NaOH, 140 mM NaCl; 2.5 mM CaCl; pH=7.4) and propidium iodide (PI, 15 µg/µl; Sigma Chemicals, St. Louis, USA). Cells were incubated in propylene tubes protected from the light, at room temperature, for one hour. The detection of apoptosis and necrosis cell percentage was determined by a flow cytometer. Cell populations as analyzed were recognized by their properties, volume (FSC) and complexity (SSC). Fluorescence in the FITC green channel was measured at 530 nm (FL-1H detector) and the red fluorescence of propidium iodide at 585 nm (FL2-H).

Calculation of the Proliferation Rate—CFSE-DA:

To characterize the proliferation activity of IBU/ASE-16 cells (CNCM I-5000), a proliferation assay was performed with the marker carboxyfluorescein (CFSE—carboxy-fluoresceindiacetate succinimidyl ester—Molecular Probes). The protocol was standardized for the use of that marker with IBU/ASE-16 cells for identifying the ideal concentration of CFSE. That marker, diluted in 0.1% human albumin in PBS under different concentrations, was added to the medium with cells for marking. The marking time was 10 minutes at 37° C., with homogenization at each 3 minutes. Marking was interrupted by adding five times the volume of L-15B medium+10% SBF, with incubation for 5 minutes on ice and in the dark. The cells were then washed 3 times with 20 ml of L-15B medium+10% SBF and re-suspended for counting. An aliquot of cells was separated to verify cell marking intensity with CFSE, on the marking day (day zero), in a flow cytometer.

Analysis of Cell Cycle Stages by Flow Cytometry:

IBU/ASE-16 cells in culture were scraped with a cell scraper, centrifuged for 10 minutes at 900 g, the supernatant was discharged and the pellet was re-suspended in a cytometry buffer (FACs Flow—BD). Cells were again centrifuged for 3 minutes at 1000 g and the supernatant was discharged. Cells were carefully re-suspended in 1 ml ethanol 70% RNAse, transferred to microtubes and stored at −20° C.

IBU/ASE-16 cells were incubated with a propidium iodide solution (1.8 mg/ml) for evaluation of DNA quantity and integrity in each cell cycle step. The distribution of cell cycle stages was evaluated by a flow cytometer. Results obtained from the acquisition program Cell-Quest, with an average of 10,000 events as acquired by the cytometer, were analyzed by the software Win MDI 2.8 and DNA content was measured for its fluorescence intensity (FL2-H). Results were expressed as an average percentage of cells distributed in the different steps of the cell cycle: fragmented DNA—apoptosis, G0/G1, S and G2/M.

Mitochondrial Electric Potential—Rhodamine 1 2 3:

For the analysis of the mitochondrial membrane potential ($\Delta\psi m$), the fluorochrome Rhodamine 1 2 3 (Invitrogen, USA) was used. Mitochondria is a cytoplasm organelle related to energy metabolism. On the internal mitochondrial membrane, the electron transporting chain is located, producing energy from the flow of electrons and consequent oxidative phosphorylation. Rhodamine 123 is a fluorescent probe received when electrons are donated to the respiratory chain.

When the electrochemical gradient is formed, Rhodamine 123 is received, and its fluorescence emission is reduced. Rhodamine 123 permeates the mitochondria membrane and inhibits transport processes, especially the electron transporting chain, delaying internal breathing.

IBU/ASE-16 cells were scraped with a cell scraper, centrifuged at 900 g for 10 minutes, the supernatant was discharged and 5 µl Rhodamine 123 (5 mg/ml) were added. Subsequently, cells were incubated in an oven at 37° C. for 30 minutes. After that period, tubes were centrifuged, the supernatant was discharged and the precipitate was re-suspended in 100 µl buffer solution for cytometry, FACs-Flow (BD). The analysis of Rhodamine 123 marking on *A. sculptum* cells was performed in a flow cytometer FACscalibur (BD), by acquiring 10,000 events. Data was analyzed by the program WinMDI 2.8.

Cell characterization by confocal microscopy:

CLSM—Confocal Laser Scanning Microscope—is an important tool in biological research, chemical and material analysis, allowing the tridimensional location of structures and molecules marked with fluorochromes. For that reason, cultures of IBU/ASE-16 cells were prepared as disclosed below.

IBU/ASE-16 cells were scraped from the flask with a cell scraper and the cell suspension was put in a 15 ml Falcon tube. After precipitation, the pellet was re-suspended with culture medium L15-B+10% SFB. The cell suspension was then distributed onto plates (Chambered≠1.0 Borosilicate Coverglass System), wherein each plate received 1.5 ml of medium.

Adhered cells (on slides) were washed twice in a PBS solution and subsequently fixed to a 4% paraformaldehyde solution for one hour. They were then washed with a TBS solution (washing buffer—0.15 M NaCl (Sigma), 20 mM Tris-HCl (Sigma) and 0.05% Tween 20 (Sigma), pH 7.4). The cell membrane was permeabilized with a 0.1% Triton X-100 solution (Sigma) in TBS. After a new sequence of washing in TBS, the cells were incubated in a bovine albumin serum solution (BSA, Sigma) at 5% in PBS for 30 minutes, for blocking unspecific markings, being then incubated with primary antibodies (Table 1) for one hour. Subsequently, they were incubated with a secondary mouse or goat anti-IgG antibody linked to fluorescein (FITC) and diluted in a 5% BSA solution in PBS at a 1:500 ratio. That incubation lasted for one hour at room temperature and cells were subsequently washed in the same TBS sequence. For negative controls, primary antibodies were substituted with PBS.

Slides were assembled over glass blades, using the specific assembly medium for immunofluorescence Vectahield with DAPI. Markers below are presented on Table 1.

Ndel (Santa Cruz): it is a protein present in the testis, brain, heart, hypothalamus, liver, lungs, spleen and stomach, specifically in the centrosome (interphase) and the spindle apparatus. It positively regulates dynein, as directed from final subtraction. Evidence suggests that Ndell interacts with LIS1 to sustain the dynein function, thus impacting the organization of microtubes, nuclear translocation and neuronal positioning. Ndel is phosphorylated during mitosis, and seems to bind dinectin and dynein to the parent centriole for anchoring microtubes. The loss of Ndel function in the neocortex under development damages neuronal positioning and uncouples centrosome and the core. Ndel may also affect mitochondrial function or transport, initiating a cascade of events which may end up in psychiatric diseases, such as lissencephaly and schizophrenia.

TABLE 1

Antibodies and concentrations as used in the assays:

| Primary antibody | Type | Origin | Dilution | Procedence |
|---|---|---|---|---|
| Ndel | Monoclonal | Mouse | 1:100 | Santa Cruz |
| ABCG2 | Monoclonal | Mouse | 1:100 | Chemicon |
| CD44 | Monoclonal | Mouse | 1:100 | Sigma |
| Nestin | Monoclonal | Goat | 1:100 | Santa Cruz |
| Beta-tubulin III | Monoclonal | Mouse | 1:100 | Sigma |
| Actinin | Monoclonal | Mouse | 1:100 | Sigma |
| Titin | Monoclonal | Mouse | 1:100 | Santa Cruz |
| Oct-3/4 | Monoclonal | Mouse | 1:100 | R&D Systems |
| Beta-I-Integrin | Monoclonal | Mouse | 1:100 | Abcam |

ABCG2 (Chemicon): Conserved transporter protein, catalyzing the transport of molecules through extracellular and intracellular membranes, by means of ATP hydrolysis energy. It is also known as a specific placenta transporter (ABC) and a breast cancer resistance protein (BCRP1). ABCG2 grants resistance for a variety of chemotherapeutic agents, including anthracyclines, mitoxantrone, bisantrene and topotecan. Under normal conditions, it may serve for protecting purposes, by removing toxins from the cell and performing an important role for the regulation of stem cell differentiation, ABCG2 is widely expressed in a large variety of stem cells, becoming an important marker for those cells, and is abundantly present in the placenta, liver, intestine and stem cells.

CD44 (Sigma): cell surface glycoprotein, involved in cell-cell interaction, and performing an important role for embryogenesis and development. It also works in hematopoiesis, activation of lymphocytes and tumor metastasis. It works as a hyaluronic acid (Ah) receptor and interacts with ligands, such as osteopontin (PN). CD44 mediates cell-cell and cell-matrix interactions, thus performing an essential role in cell adherence and cell migration. CD44 has an alternative domain for splicing events and is expressed in many isoforms known as CD44R, CDw44, CD44S, CD44H (hematopoietic) and CD44E (epithelial). While most of these isoforms are expressed in tissues through the body, one specific isoform, known as CD44H, is expressed in high levels in cancer tissues, suggesting an important role for that protein in tumor progression.

Nestin (Santa Cruz): it is a protein with a large intermediate filament (IF) 200220 kDa of parent cells for embryo CNS. It is also a constituent of the dynamic network IF, during muscle development, when it is polymerized with Desmin and Vimentin. Nestin, jointly with Vimentin or a-Internexin, forms heterodimeric molecules. The exclusion of IF domain changes nestin localization in CNS precursor cells and radial glial cells in in vivo models. Nestin is a marker for neuroepithelial stem cells, glioma cells and tumor endothelial cells during their quick growing. During axon elongation in neuron differentiation, that protein is located in the growth of cones and should perform a role in the growth and direction of these cones. In rat adrenal glands, nestin is expressed by the fasciculata zone and by the reticular zone. It is also expressed by dermatomal cells and by myoblasts during the first stages of myogenesis.

Beta-Tubulin III (Sigma): it is the largest constituent of cytoskeleton, having five distinct forms, known as a, b, g, d and tubulin. Forms a and b bind themselves in heterodimers and constitute a microtube filament. Multiple isoforms of b tubulin (b1, b2, b3, b4, b5, b6 and b8) were characterized and expressed in mammal tissues. b1 and b4 are found in the cytoplasm, b2 is present in cores and nucleoplasm and b3 is a neuron-specific cytoskeleton protein. g Tubulin forms gammasome, which is required for nucleation of microtube filaments in the centrosome. Both d tubulin and e tubulin are linked to the centrosome. d Tubulin is a homolog of d tubulin Uni3 from Chlamydomonas and is found in association with centrioles, considering that e tubulin locates the pericentriolar material. e Tubulin shows a location-specific cell cycle pattern; firstly, associating just the older centrosome in a recently duplicated pair and later associating two centrosomes.

Actinin (Sigma): also known as a-actinin. There are four specific a-actinin tissues, i.e. a-actinin-1, a-actinin-2, a-actinin-3 and 4-a-actinin, which are located for muscle and non-muscle cells, including skeleton, heart and smooth muscle cells, as well as inside the cytoskeleton. Each a-actinin protein contains an actinin link domain, two homologous calponin domains, two EF domains and four spectrin repetitions. Through these linking domains, working as protein aggregation, they may be crosslinked to F-Actin, anchoring actin to a variety of intracellular structures.

Titin (Santa Cruz): also known as connectin, it is a large protein involved in the time and space control of formation of sarcomeres (contractile units) highly ordered in the striated muscle. Besides assembling sarcomeres, titin also works to keep the structural integrity of myofibrils inside the muscle, and to organize machinery in chromosome condensation for cell division. Titin is a giant protein, constituted by 27,000 amino acids, having a catalytic domain of self-regulated serine kinase, with a link region for calcium/caldomoduline, which are involved in its activation. Activated titin phosphorylates the protein telethonin in the muscle, a protein which is abundant in the heart and skeleton muscle, entailing titin activity in cytoskeleton reorganization during myofibrilogenesis.

OCT-3/4 (R&D Systems): Oct-3/4 is a POU transcription factor expressing embryo stem cells and germinative cells. Its expression is required to sustain cell pluripotency and self-renovation. Oct-3/4 is the best known marker for totipotent embryo stem cells.

Beta Integrin—I (Abcam): Integrins are transmembrane proteins linked to the proteins included in intracellular complexes which, on the other hand, are linked to the cytoskeleton. Integrins form heterodimers constituted by an alpha and a beta subunit and, so far, 18 alpha subunits and 8 beta subunits are known in mammals. These proteins are membrane receptors involved in cell adherence and in the recognition of a variety of processes, including embryogenesis, homeostasis, tissue repair, immune response and metastatic spreading of tumor cells. Beta integrin, also known as CD29, is a protein which, in humans, is coded by the gene ITGB1. It is an integrin unit linked to very late antigen receptors. We know that it is conjugated to subunit alpha-3 to create an a3β1 complex reacting with molecules, such as netrin-1 and reelin. A minimum of 100 cells of *A. sculptum* was analyzed by reaction, so to observe reaction positivity. Acquisition and analysis of results were made through confocal (Zeiss LSM 510 Meta, Carl Zeiss, Germany, using 488 nm as excitation laser for FITC). Images were analyzed and treated by using the program Zeiss LSM Image Browser (Version 4.2.0.121, Carl Zeiss MicroImaging GmbH, Germany).

Scanning Electron Microscopy (SEM):

Samples of IBU/ASE-16 cells were fixed to 3% glutaraldehyde for 24 h, thus allowing for protein penetration and precipitation, assuring ideal preservation of the ultrastructure. After that period, samples were washed in a buffer solution of cacodylate for five times and post-fixed to a 4% OsO$_4$ buffer solution for 1 h, being again washed in a buffer solution. The cell suspension was centrifuged at 900 g for five minutes, re-suspended in L-15B medium supplemented with 10% SFB and cultivated on 2 cm$^2$ Petri plates, under 10$^6$ cell/ml density. Samples were transferred to permeable baskets in the drying set (critical point—BalTec) and subsequently dehydrated in double baths of alcohol under the concentrations: 30, 50, 70, 80, 95 and 100%. Various exchanges were required to assure full water removal. Sample drying was performed in the critical point device, using carbonic gas, and the plates received metal cover with gold by means of cathodic spraying (sputtering). After the end of the process, the material was analyzed by the scanning electron microscope Philips XL30.

Tumorigenesis Assay:

For that assay, three nude Balb-C mice (mouse 1 weighing 21.98 g, mouse 2 weighing 25.75 g and mouse 3 weighing 20.7 g) were used. IBU/ASE-16 cell suspension was prepared (1 ml) and inoculated with an insulin syringe under the concentration of 106/point of application. Four inoculation points were marked on the back of each animal. 0.1 ml of the cell suspension was injected at each point. Mice have been observed daily, up to 120 days after inoculation.

Cell Growth Evaluation: Growth Curve.

To evaluate the cell expansion and replication capacity, standardize the ideal cell concentration for cell growth and evaluate its kinetic behavior, growth curves will be prepared. After the initial establishment of the IBU/ASE-16 culture, not changing previous environmental conditions, samples will be obtained after 24, 48, 72, 96, 120, 144 and 168 hours. The evaluation of the number of cells and their viability will be performed by means of cell counting in a Neubauer chamber, with the help of 0.2% (v:v) Tripan blue pigment. This process will be performed in triplicate.

Proteomics:

The term proteomics was initially introduced in 1995 and defined as being the large scale characterization of the set of proteins expressed in a cell or tissue (WILKINS et al, 1997). That set of expressed proteins in a cell or tissue from the genome is called proteome. The proteome of an organism reflects the set of proteins expressed by that organism in a given situation and, in opposition to the genome, is not static, and cannot be modified, depending on the conditions and stimuli to which that organism is exposed.

Therefore, proteome reflects the expression of molecules with more direct influence over biochemistry and cell operation. The same kind of cell may present different proteomes in response to the action of drugs, pathogen infection, pollution and different kinds of abiotic stress.

Proteomics aim to study the structure, function and control of biological systems by analyzing various properties of proteins, also including sequence studies (identity), abundance, activity and structure of proteins as expressed by a cell, as well as the modifications suffered by proteins (WILLIAMS & HOCHSTRASSER, 1997).

Data generated by proteomic analysis allow to reach different purposes, such as:

a. clarify which proteins are involved in metabolic routes as related to different cell processes;

b. identify new pharmacological targets and biological arkers, related to the process of disease onset and progression;

c. identify bioactive molecules from natural biological extracts, causing the development of new pharmaceuticals; and d. characterization of cell responses to given drugs, diseases and environmental changes.

Despite the concept of proteome being relatively new, this study uses protein separation skills which have already been developed for a long time, such as bidimensional electrophoresis (O'Farrel, 1975). However, its use in proteome analysis was limited, due to the low reproduction ability of gels and to the lack of sensitive methods to identify separate proteins.

Electrophoresis consists in separating, under the influence of an electric field, cargo-bearing molecules. The speed of migration depends on factors such as: size, shape and electric charge of the molecule being studied. In two-dimension electrophoresis, proteins are submitted to two consecutive steps of electrophoretic separation, based on the different properties of proteins.

The first step of separation, known as first dimension, consists of isoelectric focusing, wherein the proteins are separated by their electric charge on a polyacrylamide gel. In this step, proteins migrate within the gel until reaching a stationary position in which their net charge is zero, which is the isoelectric point of the protein.

In the second dimension, proteins as previously separated by isoelectric focusing are submitted to denaturing electrophoresis on polyacrylamide gel (SDS-PAGE), wherein they are separated according to their molecular masses. Since the parameters used in the first dimension (isoelectric point) and the second dimension (molecular mass) are independent, the separation reaches high level of resolution, thus allowing to visualize hundreds of different proteins at the same time.

After two-dimension electrophoresis, proteins are directly visualized in the gel, by means of dyeing methods with Comassie blue or by silver dyeing, resulting in a two-dimension profile of spots, each one containing multiple copies of a protein. The identification of proteins as present in the two-dimension electrophoresis profiles is made by mass spectrometry. This consists of analytical skills for molecule studies based on the ionic movement in electric and magnetic fields, so to classify them according to their mass-charge ratio, producing mass spectrum.

Mass spectrometry has already been used for many years for the study of inorganic molecules, but only in the last decade it was improved for the study of biological molecules (proteins), without its destruction during the ionization process (YATES, 1998). The improvement of these two-dimension electrophoresis skills and mass spectrometry enabled the enhancement in protein studies in large scale and the creation of the concept of proteome analysis (TYERS & MANN, 2003).

Two-dimension electrophoresis covers five steps: (a) sample preparation; (b) first dimension (isoelectric focusing); (c) second dimension (denaturing electrophoresis on polyacrylamide gel); (d) protein detection; and (e) digitalization and image analysis.

Sample preparation: the sample of IBU/ASE-16 cells for two-dimension electrophoresis will be initially prepared with the extraction, precipitation and solubilization of proteins. The extraction will be performed with 40 mM Tris-HCl buffer, pH 7.0, 250 mM sucrose, 1% Tritin X-100, 10 mM EDTA, 1 mM DTT and 1 mM PMSF. Protein precipitation at −20° C. will be performed with 10% trichloroacetic acid in acetone, and its re-solubilization in a 7 M urea solution, 2 M thiourea, 4% CHAPs, 2% IPG buffer and 65 mM DTT.

First dimension (isoelectric focusing): the isoelectric point (pi) of a protein corresponds to a pH value wherein the sum of all partial loads is zero, Said property depends on the ionic strength, the nature of the used buffer and any other solute included in the medium, but does not depend on protein concentration. The isoelectric point of a protein is given by a technique known as isoelectric focusing (electrofocusing), consisting of electrophoretic separation, wherein proteins are separated according to the differences in their isoelectric points. Once submitted to an electric field, proteins will migrate until they find a pH range relative to its pi, and there they will have full neutral charge, interrupting migration in the gel (BERKELMAN & STENSTED, 1998).

Second dimension (denaturing electrophoresis on polyacrylamide gel).

Detection of Proteins:

Digitalization and Metabolomic Image Analysis:

The development of analytical techniques enabling to determine and quantify constituents of the intermediate metabolism is useful for the understanding of various biological processes involved in the maturation, differentiation and physiopathological processes.

Metabolomics refers to the study of the global metabolism of small molecules as present in cells, tissues, organs and biological fluids. It has the potential to significantly contribute to biomedical and biotechnological investigation. Analytical skills using nuclear magnetic resonance (NMR) have been a key tool for metabolic analysis.

The structural determination of known metabolites, using various NMR dimensional methods (1D) and (2D), is direct, and thus practically there is no need of authentic standards.

NMR is a particularly powerful detection system for the structural determination of metabolites, including atomic positions of the atoms, being highly specific. It can separately obtain data from $^{13}C$, $^{15}N$ or $^{21}H$, which are used as probes.

NMR, when required, may disclose correlation spectra between these probes, showing connections between atoms at long and short distance, thus providing, like in X ray, the design of the molecular structure and its isomers generated during tracking studies.

NMR's high power to map pure substances or even complex mixtures may provide detailed maps for biochemical routes or networks, which can, on the other hand, also serve as key entries for quantitative flow analysis.

Acquisition of $^1H$, $^{13}C$ and $^{31}P$ NMR Spectra:

$^1H$, one and two-dimension experiments will be acquired by a Bruker Avance III spectrometer, operating at 400.13 MHz for $^1H$, provided with a 4 mm high resolution probe under rotation at the magical angle (High Resolution Magic Angle Spinning—HRMAS) with triple resonance (HCP).

Spectrum Acquisition Protocol:

Basically, suppression experiments with double signal for solvent and water will be used, via continuous wave, and pulsed field gradients, besides 1D sequences using adiabatic methodologies in their pulse sequences.

HRMN for IBU/ASE-16 Cells Kept in Culture:

High resolution NMR potential will be evaluated, jointly with multivariate analysis, to find consistent correlations between the composition of IBU/ASE-16 samples, determining metabolic differences on the $5^{th}$, $15^{th}$ and $25^{th}$ days. After performing cell cultures, cells will be frozen in liquid nitrogen, processed and analyzed by NMR spectroscopy, with the use of 1D sequences with double saturation, T2 filter and $^1H$ and $^{31}P$ spectra were prepared. Data will then be processed by the program TopSpin® and signal identification and characterization will be initiated.

Figure 1:
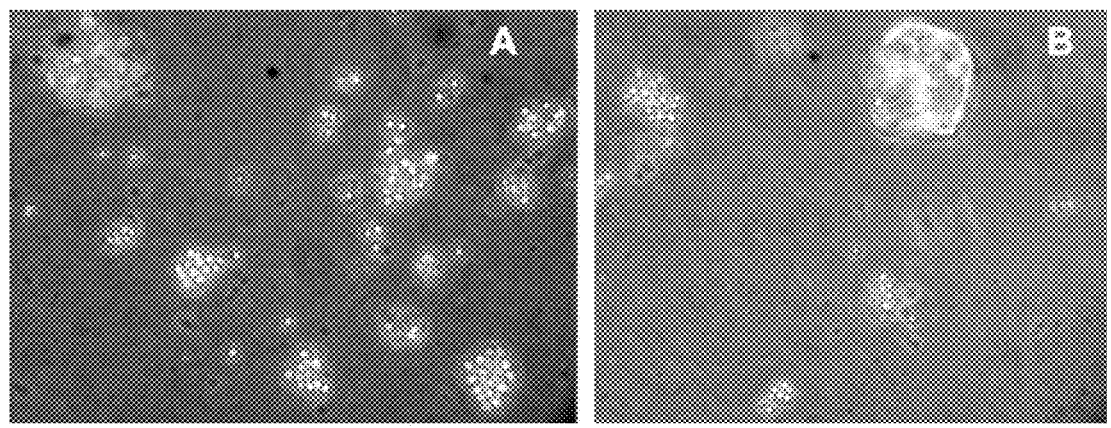

Results:

L-15B Medium Efficiency:

With the exception of the L-15B medium, the other media tested for cell growth have shown that cells may survive for a few days (3-4 days) on culture plates, but always in suspension (FIG. 1).

Figure 2:
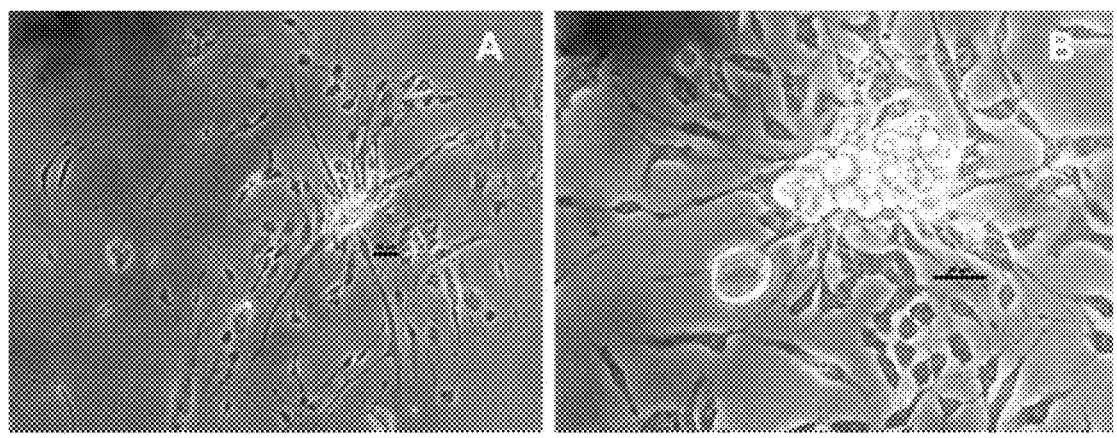
Figures 3, 4:
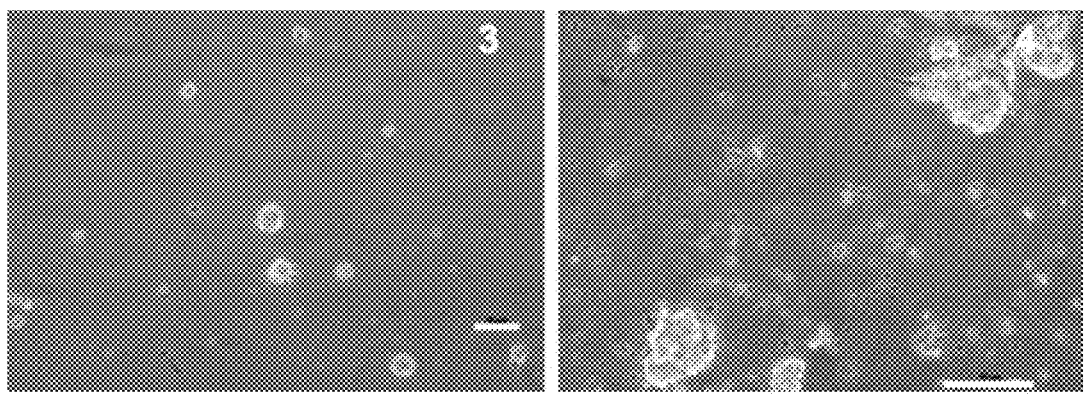
Figure 5:
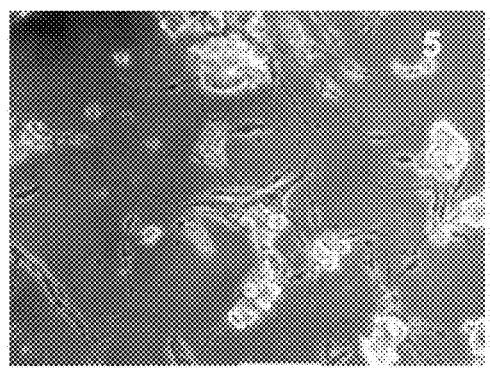
Figure 6:
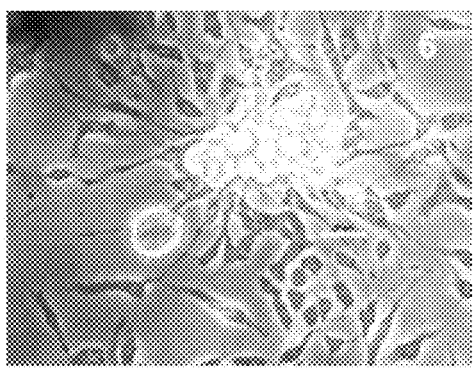
Figure 7:
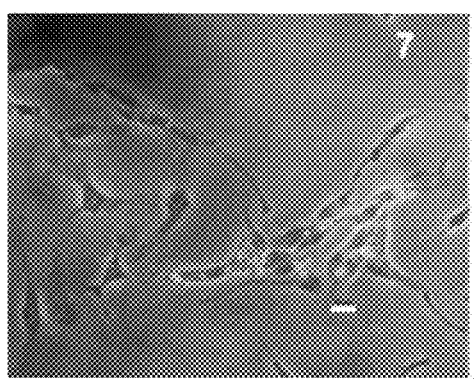
Figure 8:
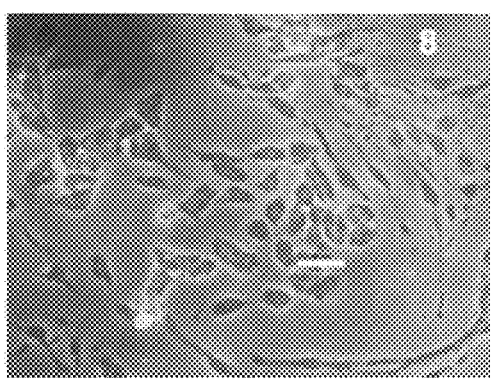
Figure 9:
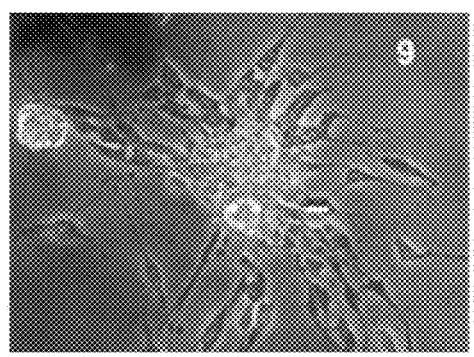
Figure 10:
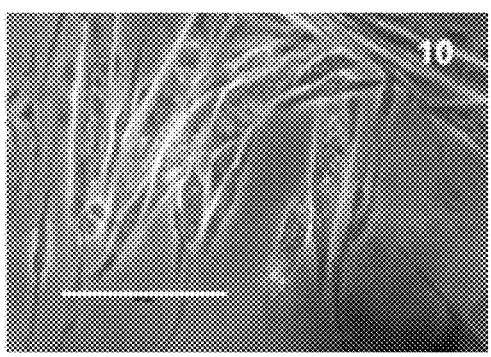
Figure 11:
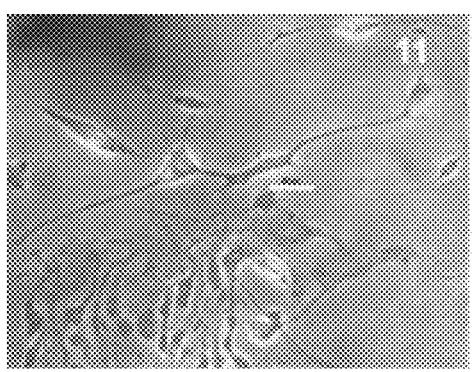
Figure 12:
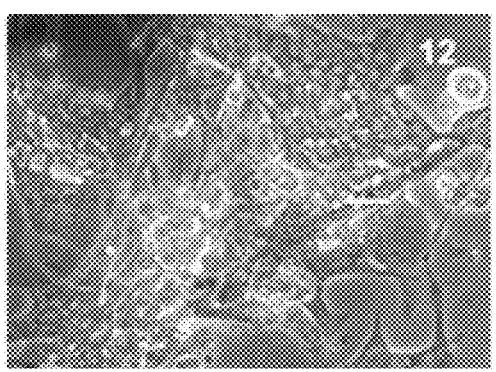

The adherence of cells to the bottom of the plate was only observed for the L-15B medium supplemented with 10% SFB (FIG. 2). For this reason, it has been chosen and used for the culture of cells of A. sculptum. We have noticed that supplementation with 20% SBF was ineffective and toxic for this kind of tick as time passed, and cells entered apoptosis after a few days.

Evaluation of the Ideal Age of the Eggs:

Among the ages of the egg masses of A. sculptum as tested, the ideal age was 21 days after the start of oviposition, to obtain the largest number of viable cells for adherence (FIGS. 3-6). We have noticed that too young eggs produce an insufficient number of cells, thus presenting adherence difficulties and forming clumps in the supernatant, which do not develop themselves. We have also verified that much older egg masses have pieces of tissue from which the cells face difficulties to migrate to the surface of the flask to be cultivated. This fact makes the adherence become difficult, with prejudice to the formation of the monolayer.

Primary Cultures:

The line of A. sculptum known as (IBU/ASE-16) was established. The acronym representing the line of A. sculptum means: the acronym of the name of the institution (IBU—Instituto Butantan), followed by the initials of the name of the species (A. sculptum), the letter "E" (simile embryos) and the number of subcultures for the first cryopreservation (16 passages).

After initiating the culture, spontaneous differentiation of IBU/ASE-16 cells was observed (FIGS. 7-12), while cell confluence increased. After two months, the first subculture became possible, with increased speed of cell growth.

Figure 13:
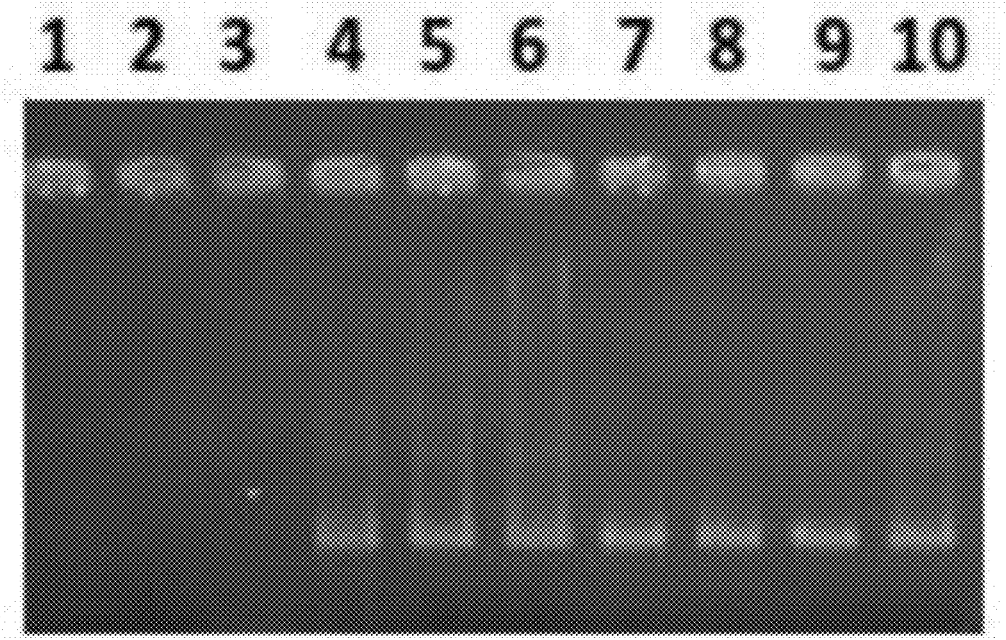

Cell Identity Confirmation:

PCR reaction to confirm the cell identity of IBU/ASE-16 (FIG. 13) was positive, and its sequence may be observed further below.

IBU/ASE-16 sequencing as obtained showed similarity in comparison with other sequences as already deposited with Genbank, according to the Blast from the partial sequence of the ribosomal 16S gene as presented by FIG. 52.

Figure 14:
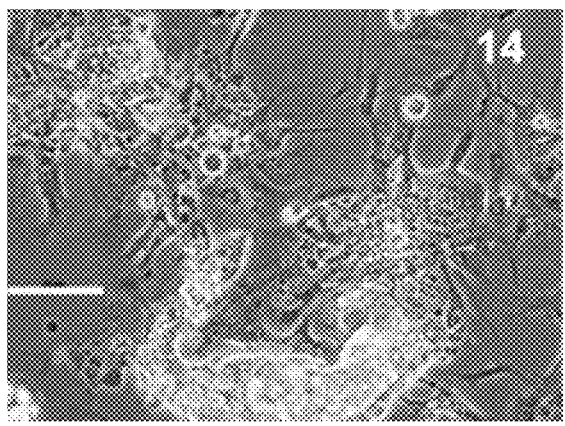
Figure 15:
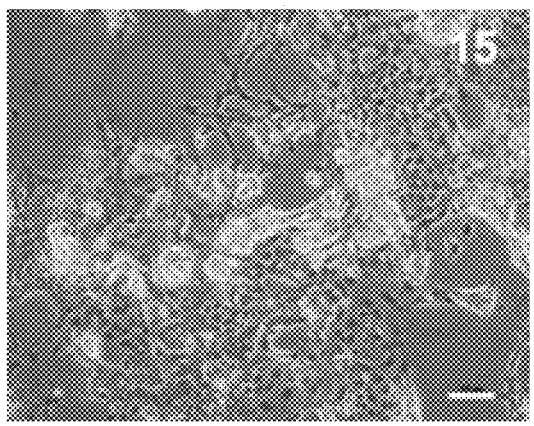
Figure 16:
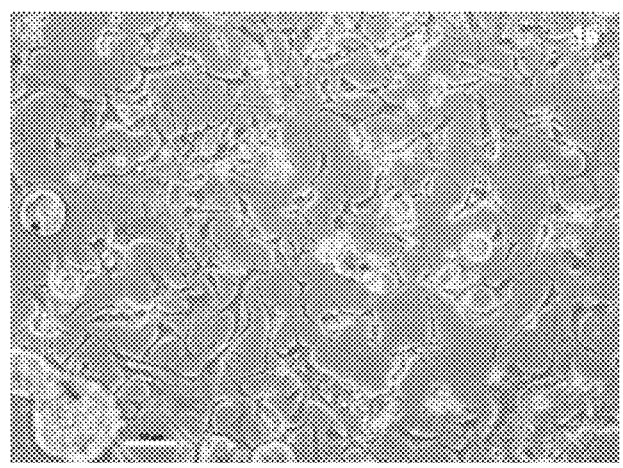
Figure 17:
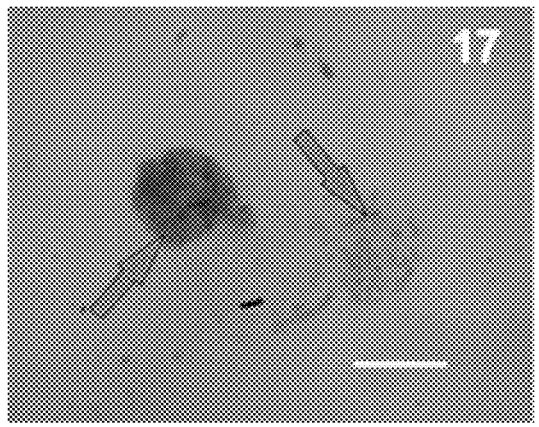
Figure 18:
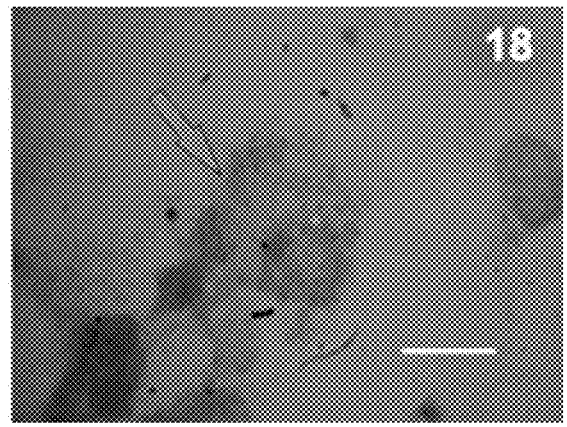
Figure 19:
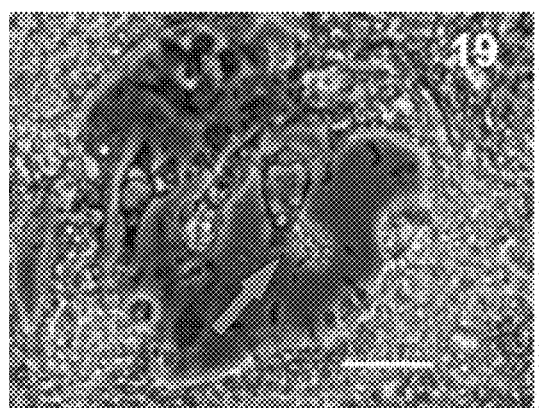
Figure 20:
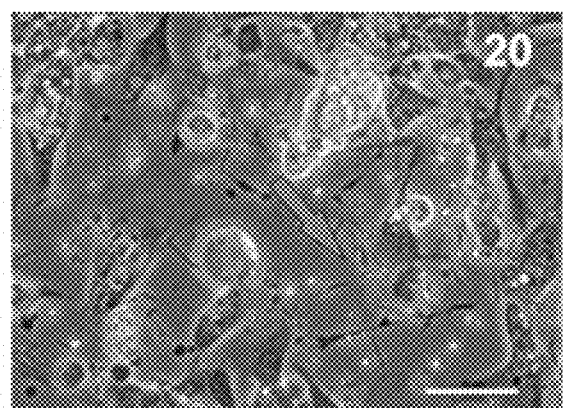
Figure 21:
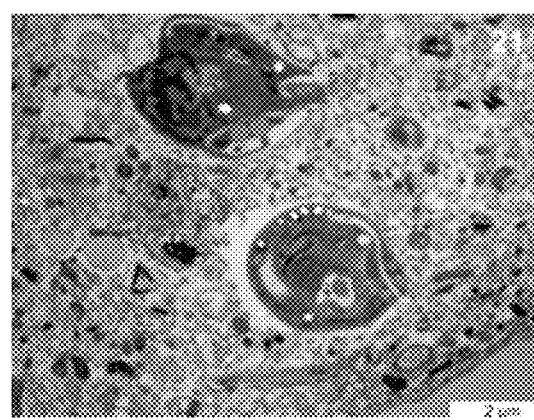
Figure 22:
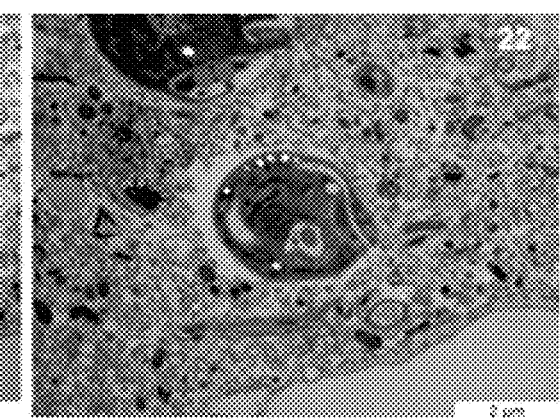
Figure 29:
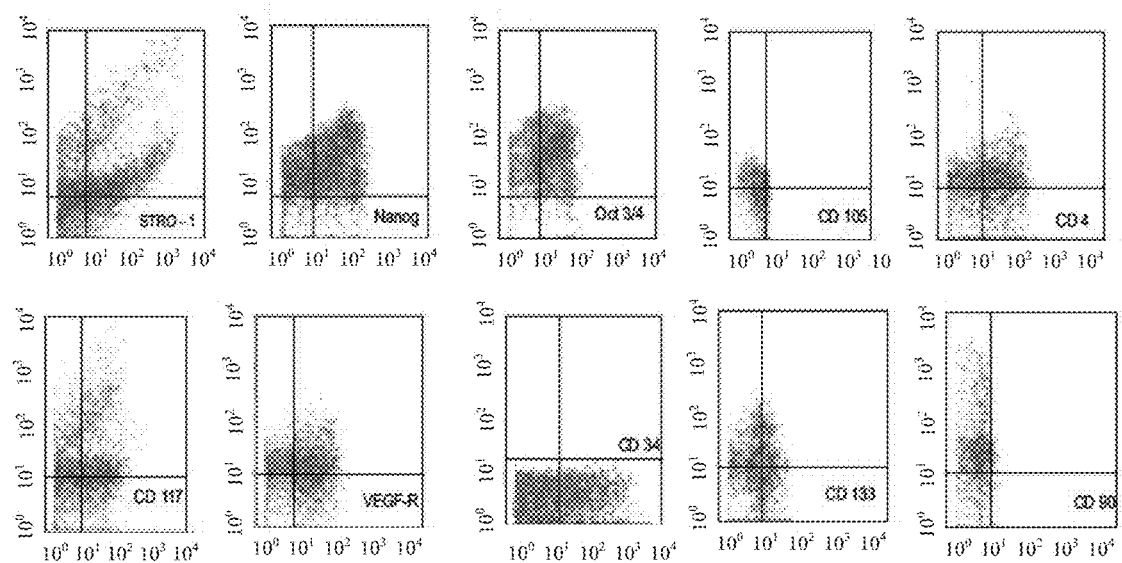
Figure 30:
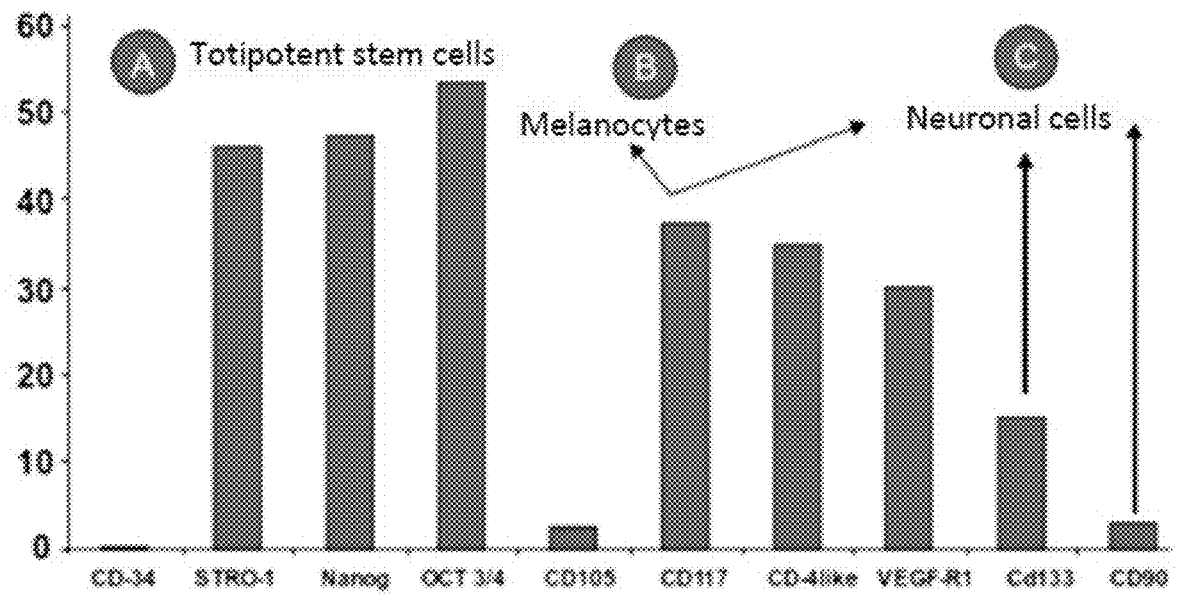
Figure 31:
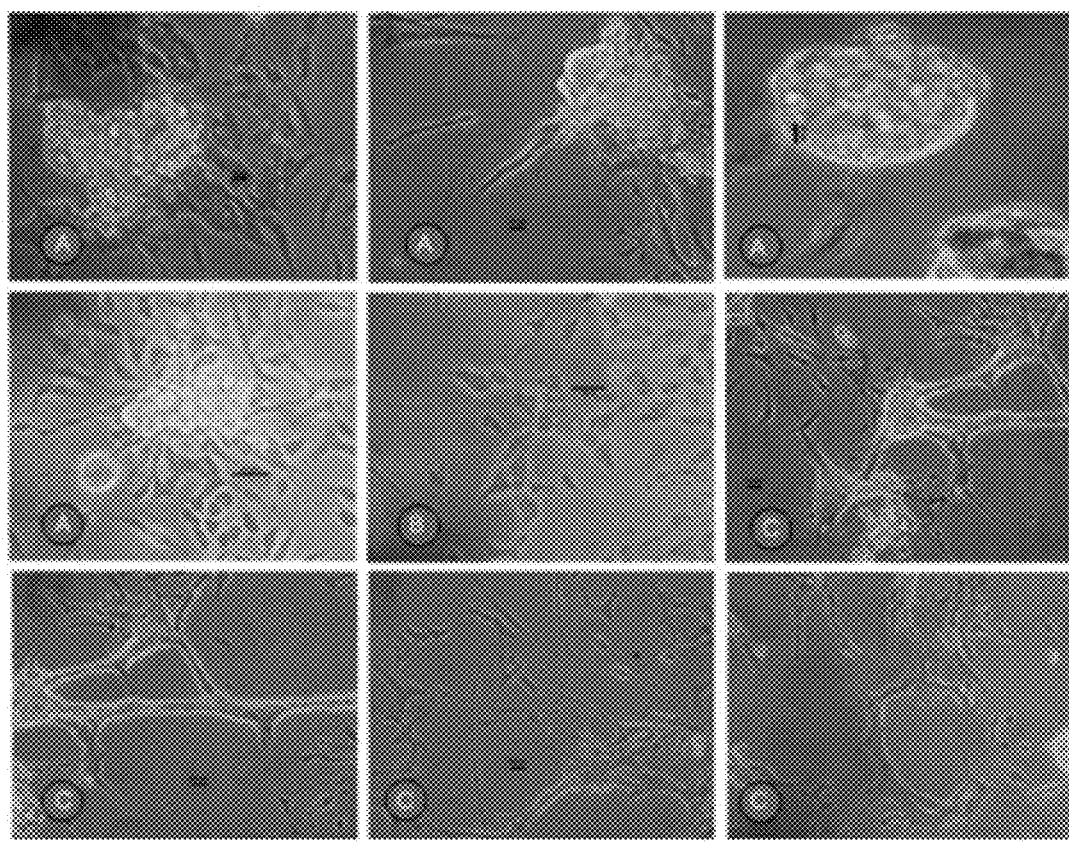
Figure 32:
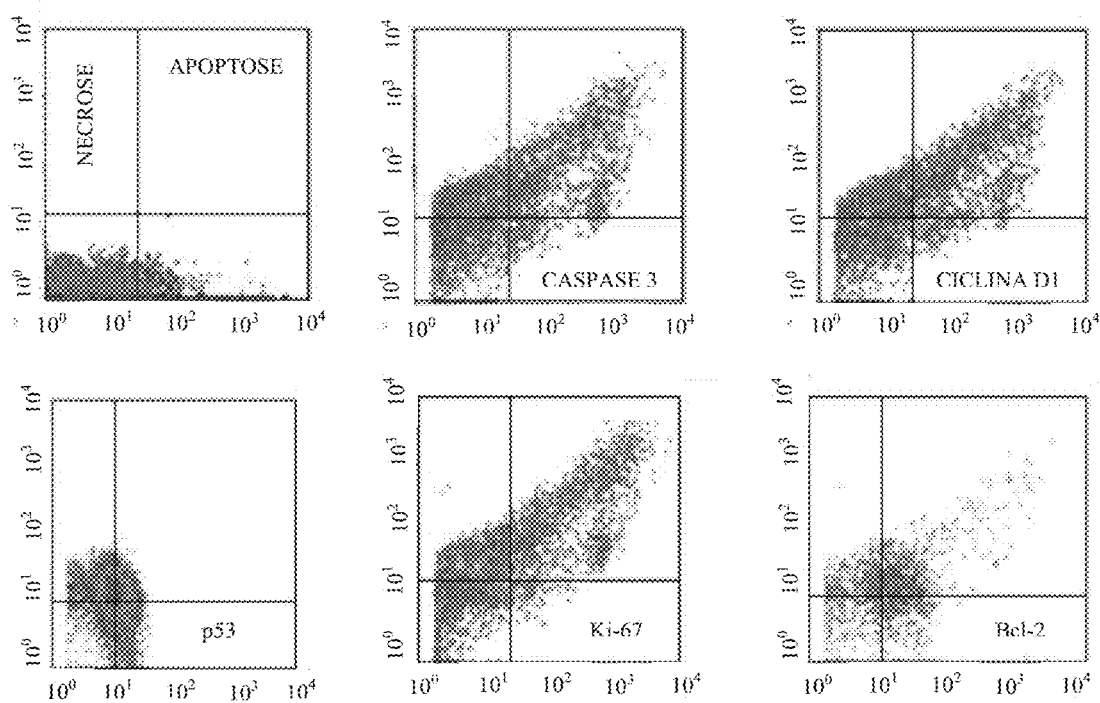
Figure 33:
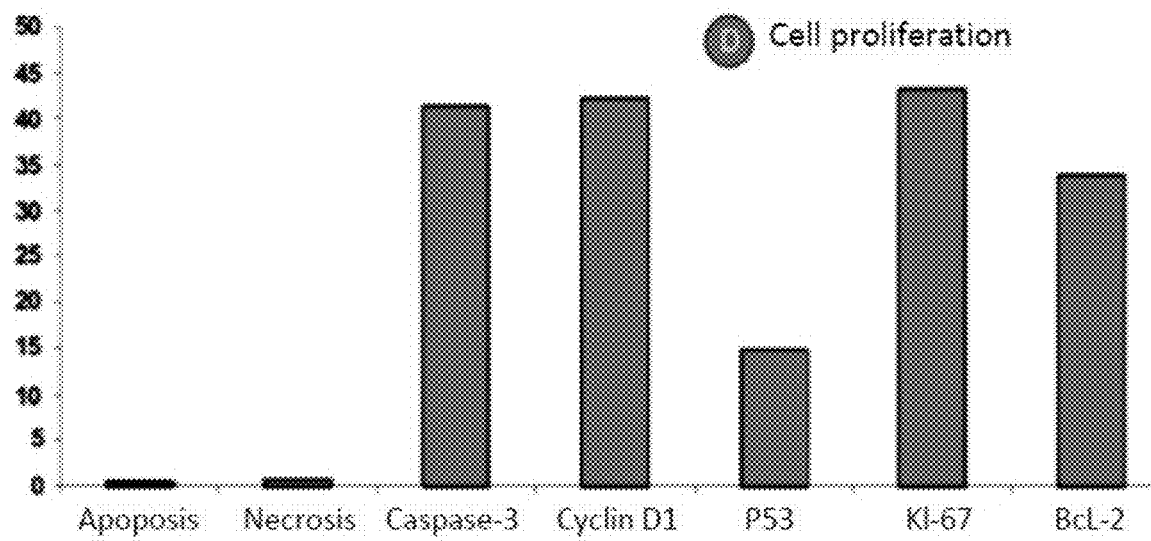
FIG. 33 is a bar graph representing the average values of apoptosis and necrosis markers, and the proliferation markers and checking points, as expressed by cells of *A. sculptum*. The results have been obtained by flow cytometer, acquired by the program CellQuestPro and analyzed by the program WINmdi 2.
Figure 34:
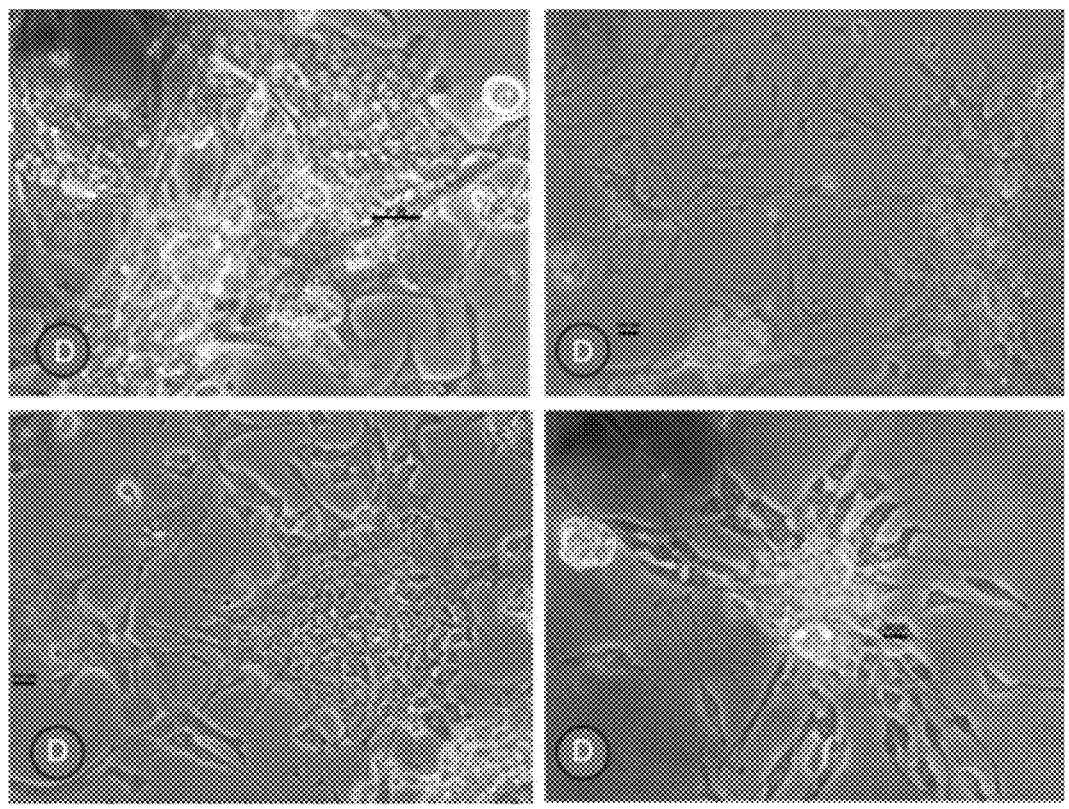
FIG. 34 shows a photomicrograph of primary cultures of cells of *A. sculptum*. D shows intense capacity of cell proliferation.

Cell Cryopreservation and Thawing:

Thawing of cells showed that cryopreservation was successful (Table 2). One culture was frozen on passage 13 and, after thawing, it was subcultured and presented excellent cell recovery. With cryopreservation and cell recovery results as shown by the table below, we can conclude that the cell line of A. sculptum (IBU/ASE-16) was established. Illustrations of the cryopreserved cultures after thawing are presented by FIGS. 14 to 16.

TABLE 2

Cryopreserved and recovered cells of A. sculptum:

| Freezing | Passage | Number of cells/ml | Thawing | Replications |
|---|---|---|---|---|
| Oct. 27, 2011 | P13 | $0.42 \times 10^5$ | Dec. 6, 2011 | P14: Jan. 20, 2012<br>P15: Feb. 23, 2012<br>P16: Mar. 12, 2012 |

TABLE 2-continued

| Cryopreserved and recovered cells of *A. sculptum*: | | | | |
|---|---|---|---|---|
| Freezing | Passage | Number of cells/ml | Thawing | Replications |
| Dec. 16, 2011 | P16 | $0.68 \times 10^5$ | Feb. 2, 2012 | P17: Mar. 1, 2012<br>P18: Mar. 12, 2012<br>P19: Mar. 26, 2012 |

Efficacy of IBU/ASE-16 as a Substrate for Microorganism Cultures:

Tests performed with the blood of patients suspected of having Lyme disease, in IBU/ASE-16 cultures, presented negative results for the growth of Borrelia spp. *A. sculptum* females artificially fed with blood from suspected patients caused oviposition from which cell cultures were obtained. Cells adhered to the bottom of the flask, as we already expected, but the growth of Spirochaetes was not verified. Concerning *Rickettsia* and protozoa, tests were successful. In case of *Rickettsia*, infection of more than 90% of used cells was found (FIGS. 17-18). Proliferation or maintenance of protozoa as tested was noticed (FIGS. 19-20), showing that the cell cultures obtained from *A. sculptum* are potential substrates for growth and isolation of said microorganisms, as well as for studies of the host-parasite interaction.

Transmission Microscopy:

FIGS. 21-24 show cell infection by *Trypanosoma*(Megatrypanum) *theileri*, penetrating IBU/ASE-16 cells. However, despite well surviving in culture, *Leishmania infantum chagasi* apparently did not penetrate IBU/ASE-16 cells (FIGS. 25-28).

Markers for stem cells, cell proliferation, regulators of the progression of cell cycle and death in IBU/ASE-16:

Markers involved with stem cells were studied by flow cytometry and confocal microscopy. Markers with better expression on IBU/ASE-16 cells by flow cytometry were: STRO-1, Nanog, OCT3/4, CD4-like, CD177, R-VEGF and CD 133, showing the potential of that cell population to present stem cells and keep itself non-differentiated and pluripotent (FIGS. 29-31). The lack of expression of the marker CD34 indicated the lack of hematopoietic parent cells and endothelial cells, in agreement with *A. sculptum* being an arthropod, and thus not having bone marrow, where those cells are found. Marker CD105 was also not expressed, indicating the non-existence, in that cell population, of endothelial cells, activated macrophages and fibroblasts. Also, the lack of expression of CD90 indicates the non-existence of stromal cells, endothelial cells and T cells.

Flow cytometry for cell population with the marking of Annexin V (Apoptosis) and PI (Necrosis) showed large variability for cells of *A. sculptum*. We have verified that the cells are not apoptotic or in process of necrosis, showing potential for their maintenance and expansion in culture. Marking with Caspase 3 showed lack of specificity concerning its expression, since cell percentages in apoptosis, $Ki\text{-}67^+$ and $Bcl\text{-}2^+$, showed its proliferative potential. However, the average expression percentage did not exceed the significant number of unviable cells, jointly with cycline D-1 and p53. High expression of cycline D1 and Ki-67 showed the large proliferative ability and control of verification points of the cell cycle of cells of *A. sculptum*, and the great variability of those cultures was made clear (FIGS. 32-34).

Proliferative Rate:

The protocol used with CSFE allowed for easy and very precise evaluation of how the marker was equally divided between the daughter cells with each cell division, CSFE has very shiny fluorescence, and thus locates cells in populations with large heterogeneity, allowing for simultaneous analysis of the cell number, position and division status. Acquisitions obtained by the flow cytometer were analyzed by the program Wizard Proliferation and are represented in the graphs below, as well as histograms representing each condition of culture (FIG. 35).

Stages of the Cell Cycle:

Cells of *A. sculptum* (IBU/ASE-16) maintained in culture for 48 hours were fixed in alcohol in RNAse and the distributions of the cell cycle stages were analyzed by flow cytometry. Results were expressed in dot plot graphs, with the average percentage of cells in the different stages of the cell cycle: fragmented DNA, G0/G1 quiescent, synthesis S stage and G2/M stage in division. Representative histograms, acquired by the analysis program ModFit, from the different stages of the cell cycle, are represented by FIG. 36.

Electric Mitochondrial Power—Rhodamine 1 2 3:

IBU/ASE-16 cells were submitted to analysis of the mitochondrial membrane potential by fluorochrome Rhodamine 123.

The technique allows to analyze the viability of cell mitochondria, providing parameters such as viable cells and/or metabolically active mitochondria, or inviable cells and/or metabolically inactive mitochondria wherein cells remain preserved, or suffer alterations leading to death. This means that the cells marked with Rhodamine 123 did not have their mitochondrial function inhibited by the link of mitochondrial membranes in electron transport.

Cells which have not been marked or have lower fluorescence intensity did not have active electron transport with consequent inhibition of the use of mitochondria.

Graphs and histograms representing the electric mitochondrial potential of IBU/ASE-16 cells, obtained by the distribution of the probe Rhodamine 123 and analyzed by the program Cell QUEST, show cell viability, illustrated by high mitochondrial activity (FIGS. 37-39).

Cell Characterization by Confocal Microscopy:

Markers expressed by IBU/ASE-16 cells by confocal microscopy were: Nestin, CD44, ABCG2, Ndel, OCT3/4, β-III tulin, titin, a-actinin and integrin β1, showing the potential from that cell population to present pluripotent stem cells compromising neural and muscle differentiation (FIGS. 40-49).

Scanning Microscopy:

With scanning electron microscopy, we could observe: cells in monolayer (A and B), division (C, D and F), intercellular junctions and connections (G, H, I and J), formation of extracellular matrix (K, M and N) and the formation of neural networks (K and L) represented by FIGS. 50-51.

Tumorigenesis Assay:

There was no growth of skin tumors in the three mice used for the tumorigenesis test. Besides confirming the non-existence of internal tumors, necropsy did not show significant changes in organs (spleen; liver, kidneys and lungs), as we can see from the average measurements as presented by Table 3.

TABLE 3

Average weights of mice and organs, and average measurements of spleens, obtained after 120 days of inoculation with cells from the line IBU/ASE-16:

| Weight of mice | Weight of spleens | Weight of kidneys | Weight of livers | Weight of lungs | Length × width of spleens (mm) |
|---|---|---|---|---|---|
| 22.81 g | 0.48 g | 0.54 g | 2.26 g | 0.39 g | 23.97 × 7.69 |

Final Remarks:

The cell line IBU/ASE-16 from *Amblyomma sculptum* (Acari: Ixodidae) is the first one to be established for a tick from the neotropical region, besides being also the first line of ticks to be characterized with biomarkers.

The isolation and characterization of different IBU/ASE-16 cell types, jointly with advancements in molecular biology (such as e.g. RNA interference technique—RNAi) and "omics" (proteomics, transcriptomics and metabolomics), open a wide range of possibilities for research, both regarding tick biology and also better understanding of the interrelations between ticks, hosts and pathogens.

Certainly, this set of knowledge will be a significant contribution to an advancement in the prevention and control of diseases spread by ticks, both to humans and animals.

Obtaining extracts for the production of vaccines and candidate recombinant proteins for biopharmaceuticals and acaricides, production of diagnostic kits for the detection of antigens for animal and human use, obtaining clones for use in genotyping, use as a substrate for the isolation and cultivation of pathogens are some of the applications of the IBU/ASE-16 cell line with its characterized cell types.

The perspective that all the above standardized procedures for line IBU/ASE-16 may also be applied to other species with medical and veterinary importance is also considered, thus allowing research of vaccine agents for the control of diseases transmitted by them.

In another embodiment, the invention provides a diagnosis method in vitro consisting of contacting the cell line as obtained by the process as defined with a sample of a body fluid from an individual.

The term "body fluid" means any liquid originating from the human body. They include fluids excreted or secreted from the body.

In another embodiment, the invention provides a pharmaceutical composition comprising the cell line as obtained by the process and a pharmaceutically acceptable carrier.

The term "pharmaceutically acceptable carrier" may be, but is not limited to an organic or inorganic excipient, be it solid or liquid, which is adequate for the selected mode of application, such as oral application or by injection, and given under the form of a conventional pharmaceutical preparation. This also includes the solid preparation, such as pellets, granules, powders, caplets and liquids, such as solutions, emulsions, suspensions and similar. Said carrier includes starch, lactose, glucose, sucrose, dextrin, cellulose, paraffin, fatty acid glyceride, water, alcohol, gum Arabic and similar. Additives, stabilizers, emulsifiers, lubricants, agglutinants, pH adjustment controllers, isotonic agents and other conventional additives may be added, if required.

In another embodiment, the invention provides an immunological composition comprising the cell line obtained by the process as already defined and an adjuvant.

The term "adjuvant" should be understood as immunopotentializing substances, which may be natural or synthetic compounds.

Therefore, despite just one embodiment of the invention has been shown, it will be understood that various exclusions, substitutions and amendments to the line of tick cells, which is provided from embryo eggs, e.g. from *Amblyomma sculptum*, of the invention can be made by an expert in the art, not infringing the spirit and scope of the invention.

It is expressly understood that all combinations of elements performing the same function, substantially in the same way, to reach the same results, are within the scope of the invention. Substitutions of elements of an embodiment disclosed for another one are also fully intended and contemplated.

It should also be understood that the drawings are not necessarily in scale, but they are just of conceptual nature. Therefore, the intention is to be limited as indicated by the scope of the attached claims.

REFERENCES

Beati et al. "*Amblyomma cajennense* (Fabricius, 1787) (Acari: Ixodidae), the Cayenne tick: phylogeography and evidence for allopatric speciation". BMC Evolucionary Biology v. 13, p. 267 (2013).

Bell-Sakyi "Continuous cell lines from the tick *Hyalomma anatolicum anatolicum*". Journal of Parasitology, v. 7, n. 6, p. 1006-1008 (1991).

Bell-Sakyi "Tick cell lines: tools for tick and tick-borne disease research". TRENDS in Parasitology, v. 23, n. 9, p. 450-457 (2007).

Bell-Sakyi et al. "Cell lines the soft tick *Ornithodoros moubata*". Experimental and Applied Acarology, v. 49, p. 209-219 (2009).

Berkelman, T & Stensted, T. "2-D electrophoresis using immobilized pH gradients: principles and methods. Edition AC (80-6429-60)". Uppsala, Sweden: Amersham Biosciences Inc., 1998, 100 p.

Bhat & Yunker "Establishment and characterization of a diploid cell line from the tick *Dermacentor parumapertus* Neumann (Acarina: Ixodidae)", Journal of Parasitology, v. 63, n. 6, p. 1092-1098 (1977).

Bucchieri et al. "Asthmatic bronchial epithelium is more susceptible to oxidant-induced apoptosis". American Journal of Respiratory Cell and Molecular Biology, v. 27, n. 2, p. 179-185 (2002).

Blouin et al. "Applications of a cell culture system for studying the interaction of *Anaplasma marginale* with tick cells". Animal Health Research Reviews, v. 3, n. 2, p. 5768 (2002).

Eide & Caldwell "A method for obtaining primary culture of dispersed embryonic tissue from de lone star tick, *Amblyomma americanum*" Annals of the Entomological Society of America, v. 66, n. 4, p. 891-893 (1973).

Esteves et al. "Cellular and molecular characterization of an embryonic cell line (BME26) from the tick *Rhipicephalus (Boophilus) microplus*". Insect Biochem. Mol. Biol., v. 38, p. 568-580 (2008).

Kessler et al, "Estabelecimento de cultura in vitro de células embrionárias do carrapato *Boophilus microplus*". Embrapa Gado de Corte, Mato Grosso do Sul v. 54, p. 1-4 (1999), Kurtti et al. "Effect of medium supplementson tick cells in culture" Journal of Parasitology, v. 68, p. 930-935 (1982).

Mattila et al. "Isolation of cell lines and a rickettsial endosymbiont from the tick *Carlos capensis* (Acari: Argasidae: Ornithodorinae)" Journal of Medical Entomology, v. 44, n. 6, p. 1091-101 (2007).

Medvedva et al, "Culture of ixodid tick embryonic cells" Meditsinskaya Parazitologiya I Parazitarnye Bolezni, v. 41, p. 39-40 (1972).

Munderloh & Kurtti. "Formulation of medium for tick cell culture". Experimentaland Applied Acarology, v. 7, p. 219-229 (1989).

Munderloh et al. "Establishment, maintenance and description of cell lines from the tick *Ixodes scapularis*" Journal of Parasitology, v. 80, n. 4, p. 533-543 (1994).

Nava et al. "Reassessment of the taxonomic status of *Amblyomma cajennense* (Fabricius, 1787) with the description of three new species, *Amblyomma tonelliae* n. sp., *Amblyomma interandinum* n, sp. and *Amblyomma patinoi* n. sp., and reinstatement of *Amblyomma mixtum* Koch, 1844, and *Amblyomma sculptum* Berlese, 1888 (Ixodids: Ixodidae)", Ticks and Tick-borne Diseases, v. 5, n. 3, p. 252-276 (2014).

O'Farrel, P. H. "High resolution two-dimensional electrophoresis of proteins". J. Biol. Chem., v. 250, p. 4007-4021 (1975).

Pudney et al. "Culture of embryonic cells from the tick *Boophilus microplus* (Ixodidae)". Journal of Medical Entomology, v. 10, n. 5, p. 493-496 (1973).

Siclari & Qin. "Targeting the osteosarcoma cancer stem cell". Journal of Orthopedics Surgery and Research, v. 5, p. 78 (2010).

Wilkins et al, "From proteins to proteomes: Large scale protein identification by twodimensional electrophoresis and amino acid analysis". Biotechnology, v. 14: 61-65 (1997).

Williams & Hochstrasser. In "Proteome Research: New Frontiers in Functional Genomics", Berlin, Springer-Verlag, pp 1-12 (1997).

Yates, J. R. III. "Mass spectrometry and the age of the proteome". J. Mass. Spectrom., v. 33: 1-19 (1998).

Tyers & Mann. "From genomics to proteomics". Nature, v. 422: 193-197 (2003).

The invention claimed is:

1. Process for the production of an embryonic stem cell line from ticks *Amblyomma sculptum*, Berlese, 1888 (Acari: Ixodidae), comprising the following steps:

a. breaking egg masses of *A. sculptum* in full L-15B medium supplemented with bovine fetal serum at a concentration of between 5 and 10%, obtaining a cell suspension;
b. centrifuging the suspension to yield a cell pellet and supernatant;
c. discharging the supernatant and re-suspending the pellet in full L-15B medium supplemented with 5 to 10% fetal bovine serum;
d. putting the resuspended pellet in culture containers and incubating at a temperature of approximately 28-34° C.;
e. performing subcultures according to cell growth optionally until the cells reach about 90% confluence;
f. cryopreserving an aliquot of cells from the subcultures; and
g. recovering cells after cryopreservation.

2. Process of claim 1, wherein the full L-15B medium supplemented with fetal bovine serum comprises L-15 with sugars and amino acids, L-Glutamine; triptose phosphate broth; lipoprotein; stock D solution; vitamin solution and 5 to 10% fetal bovine serum.

3. Process of claim 1, wherein the full L-15B medium supplemented with fetal bovine serum further comprises antibiotics and antimicotics.

4. Process of claim 1, wherein cryopreserving step (f) comprises re-suspendeding the aliquot of cells in a full culture medium L-15B supplemented with 20% fetal bovine serum and 10% dimethyl sulfoxide (DMSO), distributing into cryopreservation containers and storing in liquid nitrogen.

5. Process of claim 4, wherein, before storage in liquid nitrogen, cells are maintained at 4° C. for 4 hours and at −80° C. for 24 hours.

6. Process of claim 1, wherein recovering step (g) comprises thawing cryopreservation containers transferring contents to containers containing full culture medium L-15B supplemented with 5-10% fetal bovine serum, which are centrifuged, followed by discharging the supernatant, resuspending the resulting pellet in full L-15B medium supplemented with 5-10% fetal bovine serum, and incubating the cells at 28-32° C.

7. Process of claim 1, wherein the egg masses in step (a) have an age of between 19 and 21 days after the start of oviposition.

8. Process of claim 1, wherein the cryopreserving step (f) is carried at about four passages.

9. Embryonic stem cell line from ticks *Amblyomma sculptum*, Berlese, 1888 (Acari: Ixodidae), produced by the process of claim 1.

10. Embryonic stem cell line of claim 9, wherein the cells express markers for stem cells.

11. Embryonic stem cell line of claim 10, wherein the markers for stem cells are one or more of OCT3/4, Nanog, STRO1, CD117, CD4-like, CD133 and VEGF-R1.

12. Embryonic stem cell line of claim 9, wherein the cells are a cell line designated as IBU/ASE-16, accession number CNCM 1-5000.

13. Process of claim 3, wherein antibiotics are penicillin, streptomycin and Amphotericin B.

14. Process of claim 1, wherein the egg masses in step (a) have an age of 21 days after the start of oviposition.

* * * * *